(12) United States Patent
Dewey et al.

(10) Patent No.: US 11,406,436 B2
(45) Date of Patent: Aug. 9, 2022

(54) BONE MATERIAL MIXING AND DISPENSING DEVICES AND METHODS

(71) Applicant: Warsaw Orthopedic, Inc., Warsaw, IN (US)

(72) Inventors: Jonathan M. Dewey, Memphis, TN (US); Daniel Shimko, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 70 days.

(21) Appl. No.: 16/944,934

(22) Filed: Jul. 31, 2020

(65) Prior Publication Data

US 2020/0360068 A1 Nov. 19, 2020

Related U.S. Application Data

(63) Continuation of application No. 16/130,025, filed on Sep. 13, 2018, now Pat. No. 10,758,287.

(51) Int. Cl.
*A61B 17/88* (2006.01)
*A61M 5/28* (2006.01)
(Continued)

(52) U.S. Cl.
CPC ...... *A61B 17/8833* (2013.01); *A61B 17/8802* (2013.01); *A61B 17/8805* (2013.01);
(Continued)

(58) Field of Classification Search
CPC . A61B 17/88; A61B 17/8802; A61B 17/8805; A61B 17/8816; A61B 17/8822;
(Continued)

(56) References Cited

U.S. PATENT DOCUMENTS 3,570,486 A 3/1971 Engelsher et al.
4,388,011 A 6/1983 Smith
(Continued)

FOREIGN PATENT DOCUMENTS

CN 106618716 A 5/2017
EP 0141912 A1 5/1985
(Continued)

OTHER PUBLICATIONS

International Search Report and Written Opinion of the International Searching Authority, Korean Intellectual Property Office, PCT/US2019/049263, dated Jan. 6, 2020.
(Continued)

*Primary Examiner* — Larry E Waggle, Jr.
(74) *Attorney, Agent, or Firm* — Sorell, Lenna & Schmidt LLP; William D. Schmidt, Esq.

(57) ABSTRACT

A device for mixing and dispensing bone material is provided. The device comprises a tubular member having an interior surface configured to receive bone material and a fluid to mix the bone material disposed within the tubular member. The tubular member is flexible and has a proximal opening configured to slidably receive a plunger, and a distal opening configured to dispense a mixed bone material from the interior surface of the tubular member. The plunger is less flexible than the tubular member. Methods of mixing and dispensing bone material are also provided.

18 Claims, 14 Drawing Sheets

(51) Int. Cl.
    *A61M 5/24* (2006.01)
    *A61B 17/00* (2006.01)
(52) U.S. Cl.
    CPC ...... *A61B 17/8816* (2013.01); *A61B 17/8822* (2013.01); *A61B 17/8825* (2013.01); *A61M 5/2425* (2013.01); *A61M 5/282* (2013.01); *A61B 2017/00893* (2013.01); *A61B 2017/00933* (2013.01); *A61B 2017/8838* (2013.01)
(58) Field of Classification Search
    CPC ............ A61B 17/8825; A61B 17/8833; A61B 2017/8838; A61M 3/0262; A61M 5/2425; A61M 5/282
    See application file for complete search history.

(56) References Cited

U.S. PATENT DOCUMENTS

| | | | |
|---|---|---|---|
| 4,411,656 A | 10/1983 | Cornett, III | |
| 4,776,704 A * | 10/1988 | Kopunek | B01F 5/0615 222/129 |
| 4,861,335 A * | 8/1989 | Reynolds | A61M 5/2448 604/88 |
| 5,015,101 A | 5/1991 | Draenert | |
| 5,370,221 A * | 12/1994 | Magnusson | A61B 17/8822 206/219 |
| 5,951,160 A | 9/1999 | Ronk | |
| 6,162,202 A | 12/2000 | Sicurelli et al. | |
| 6,332,876 B1 | 12/2001 | Poynter et al. | |
| 6,431,743 B1 | 8/2002 | Mizutani et al. | |
| 6,550,957 B2 | 4/2003 | Mizutani et al. | |
| 6,733,477 B2 | 5/2004 | Cowan et al. | |
| 6,866,039 B1 | 3/2005 | Wright et al. | |
| 7,775,399 B2 * | 8/2010 | Wood | B65D 83/0072 222/94 |
| 8,366,656 B2 * | 2/2013 | Madin | A61M 5/3148 604/185 |
| 8,534,950 B2 | 9/2013 | Sylvester | |
| 8,845,578 B2 | 9/2014 | Sherman et al. | |
| 9,067,711 B2 | 6/2015 | Melia | |
| 9,119,919 B2 | 9/2015 | Manke et al. | |
| 9,352,121 B2 | 5/2016 | Groves et al. | |
| 9,408,650 B2 * | 8/2016 | Brahm | A61B 17/8802 |
| 9,737,664 B2 | 8/2017 | Gardner et al. | |
| 2001/0037091 A1 | 11/2001 | Wironen et al. | |
| 2008/0039855 A1 * | 2/2008 | Lambert | A61B 17/8822 606/93 |
| 2016/0089216 A1 * | 3/2016 | Muller | A61M 5/2425 433/90 |
| 2017/0252715 A1 | 9/2017 | Vogt et al. | |

FOREIGN PATENT DOCUMENTS

| | | |
|---|---|---|
| EP | 0179054 | 2/1990 |
| JP | 10314181 A | 12/1998 |
| JP | 2002291842 A | 10/2002 |
| WO | 9522402 A1 | 8/1995 |
| WO | 2014130953 A1 | 8/2014 |

OTHER PUBLICATIONS

European Search Report dated May 23, 2022 by the European Patent Office in corresponding European application No. 19860522.2 for Bone Material Mixing and Dispensing Devices and Methods.

* cited by examiner

BONE MATERIAL MIXING AND DISPENSING DEVICES AND METHODS

BACKGROUND

The use of bone material including natural bone and bone substitute materials for filling a bone repair site is often used in orthopedic medicine. While bone wounds can regenerate without the formation of scar tissue, fractures and other orthopedic injuries take a long time to heal, during which time the bone is unable to support physiologic loading without the use of implantable medical devices. Metal pins, screws, rods, plates and meshes are frequently required to replace the mechanical functions of injured bone. However, metal is significantly more stiff than bone. Use of metal implants may result in decreased bone density around the implant site due to stress shielding. Physiologic stresses and corrosion may cause metal implants to fracture. Unlike bone, which can heal small cracks through remodeling to prevent more extensive damage and failure, damaged metal implants can only be replaced or removed. The natural cellular healing and remodeling mechanisms of the body coordinate removal of bone and bone grafts by osteoclast cells and formation of bone by osteoblast cells.

Conventionally, bone tissue regeneration is achieved by filling a bone repair site with a bone material (e.g., bone graft). Over time, the bone material is incorporated by the host and new bone remodels the bone material. A bone material can be made from various components such as bone particulates alone or combined with additive materials. However, handling of the bone material, including mixing it with different components and dispensing it can be difficult to reduce waste and introduction of containment into the bone material can occur.

Currently, there are various delivery instruments used for bone material dispensing, however, these instruments do not mix and also deliver the bone material. For example, a user (e.g., surgeon) can mix the bone material with liquid components in a bowl before the bone material is loaded into a dispensing instrument. However, the use of a bowl can create a messy and non-sterile environment, often leading to waste especially when transferring the bone material to a dispensing instrument. Further, by using separate instruments to mix and dispense the bone material, the amount of time the bone material can be administered to the patient is prolonged.

Therefore, it would be beneficial to provide devices for effectively mixing and dispensing bone material. It would also be beneficial for a user to be able to mix the bone material in the device via a flexible body such that mixing can be done just prior to dispensing. Methods and kits for mixing and dispensing bone material would also be beneficial.

SUMMARY

Devices and methods are provided for mixing and dispensing bone material. In one embodiment, a device for mixing and dispensing bone material is provided. The device comprises a tubular member having an interior surface configured to receive bone material and a fluid to mix the bone material disposed within the tubular member. The tubular member is flexible and has a proximal opening configured to slidably receive a plunger, and a distal opening configured to dispense a mixed bone material from the interior surface of the tubular member. The plunger is less flexible than the tubular member.

In some embodiments, a device for mixing and dispensing bone material is provided. The device comprises a tubular member having an interior surface configured to receive bone material and a fluid to mix the bone material disposed within the tubular member. The interior surface comprises a frangible barrier. The frangible barrier is configured to separate the bone material from the fluid and to break to allow mixing of the fluid with the bone material. The tubular member is flexible and has a proximal opening configured to slidably receive a plunger, and a distal opening configured to dispense a mixed bone material from the interior surface of the tubular member. The tubular member is less flexible than the frangible barrier.

In some embodiments, a method of mixing and dispensing bone material is provided. The method comprises employing a device comprising a tubular member having an interior surface configured to receive bone material and a fluid to mix the bone material disposed within the tubular member, the interior surface containing the bone material and the fluid separated by a frangible barrier disposed on the interior surface, the frangible barrier configured to break and allow mixing of the fluid with the bone material, the tubular member being flexible and having a proximal opening configured to slidably receive a plunger, and a distal opening configured to dispense a mixed bone material from the interior surface of the tubular member, the tubular member being less flexible than the frangible barrier; inserting the plunger into the proximal opening of the tubular member; inserting fluid into the tubular member at the distal opening; breaking the frangible barrier with the plunger; kneading the tubular member to mix the bone material and the fluid to create a mixed bone material; and moving the plunger in a downward direction toward the distal opening of the tubular member to dispense the mixed bone material.

While multiple embodiments are disclosed, still other embodiments of the present application will become apparent to those skilled in the art from the following detailed description, which is to be read in connection with the accompanying drawings. As will be apparent, the present disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE FIGURES

The present disclosure will become more readily apparent from the specific description accompanied by the following drawings.

Figure 1:
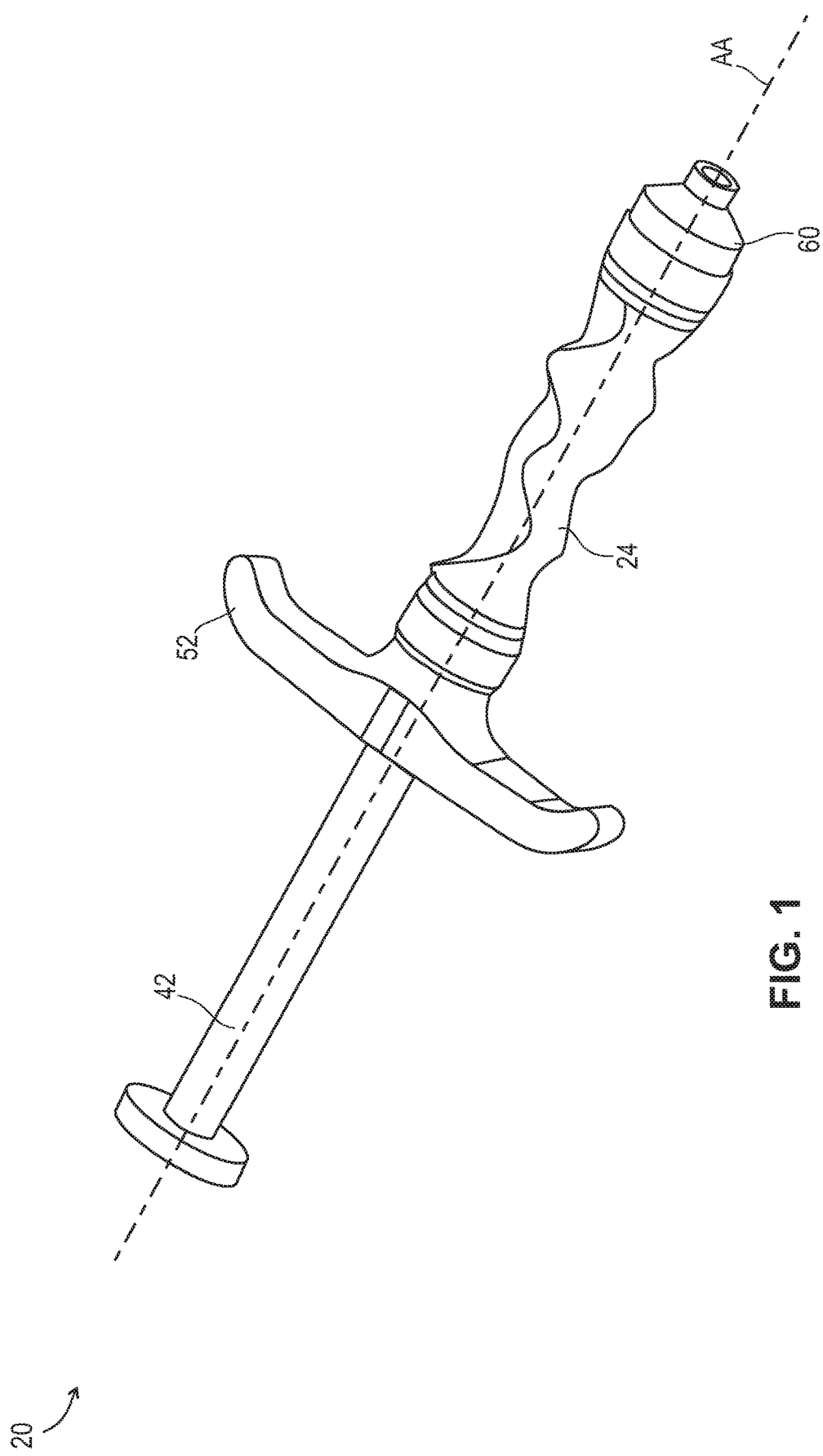
FIG. 1 is a perspective view of one embodiment of a device for mixing and dispensing bone material. The device comprises a tubular member having an interior surface configured to receive bone material and a fluid to mix the bone material disposed within the tubular member. The tubular member is flexible and has a proximal opening configured to slidably receive a plunger, and a distal opening configured to dispense a mixed bone material from the interior surface of the tubular member. The plunger is less flexible than the tubular member.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Similarly, when values are expressed as approximations, by use of the antecedent "about," it will be understood that the particular value forms another embodiment that is +/− 10% of the recited value. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Notwithstanding that the numerical ranges and parameters setting forth the broad scope of this application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, for example, 5.5 to 10.

Biocompatible, as used herein, is intended to describe materials that, upon administration in vivo, do not induce undesirable long-term effects.

Bone material includes material derived from natural bone and/or synthetic bone. Synthetic bone includes, but is not limited to biomaterials that contain hydroxyapatite, calcium phosphate, silicate materials, cements, polymers, collagen sheets, fibers, granules, alginate, starch, and/or PLGA. In some embodiments, the bone material can be ceramic/synthetic bone void fillers and can contain animal derived collagen elements. In some embodiments, various MasterGraft® products produced by Medtronic Sofamor Danek, Inc., Memphis, Tenn. can be used as the bone material.

The bone material can be in particulate form such as, for example, chips, fibers, powder or a combination thereof. Bone, as used herein, refers to bone that is cortical, cancellous or cortico-cancellous of autogenous, allogenic, xenogenic, or transgenic origin.

Demineralized, as used herein, refers to any material generated by removing mineral material from tissue, for example, bone tissue. In certain embodiments, demineralized bone material may be added to the bone void filler. The demineralized bone material described herein include preparations containing less than 5%, 4%, 3%, 2% or 1% calcium by weight. Partially demineralized bone (for example, preparations with greater than 5% calcium by weight but containing less than 100% of the original starting amount of calcium) is also considered within the scope of the disclosure. In some embodiments, partially demineralized bone contains preparations with greater than 5%, 10%, 15%, 20%, 25%, 30%, 35%, 40%, 45%, 50%, 55%, 60%, 65%, 70%, 75%, 80%, 85%, 90%, 95%, 96%, 97%, 98% or 99% of the original starting amount of calcium. In some embodiments, demineralized bone has less than 95% of its original mineral content. In some embodiments, demineralized bone has less than 95%, 90%, 85%, 80%, 75%, 70%, 65%, 60%, 55%, 50%, 45%, 40%, 35%, 30%, 25%, 20%, 15%, 10%, or 5% of its original mineral content. Demineralized is intended to encompass such expressions as "substantially demineralized," "partially demineralized," "superficially demineralized," and "fully demineralized." In some embodiments, part or all of the surface of the bone can be demineralized. For example, part or all of the surface of the bone material can be demineralized to a depth of from about 100 to about 5000 microns, or about 150 microns to about 1000 microns. In some embodiments, part or all of the surface of the bone material can be demineralized to a depth of from about 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950 to about 5000 microns. If desired, the bone material can comprise demineralized material.

Partially demineralized bone is intended to refer to preparations with greater than 5% calcium by weight but containing less than 100% of the original starting amount of calcium. In some embodiments, partially demineralized bone comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% of the original starting amount of calcium.

In some embodiments, the demineralized bone may be surface demineralized from about 1-99%. In some embodiments, the demineralized bone is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% surface demineralized. In various embodiments, the demineralized bone may be surface demineralized from about 15-25%. In some embodiments, the demineralized bone is 15, 16, 17, 18, 19, 20, 21, 22, 23, 24 and/or 25% surface demineralized.

Demineralized bone matrix (DBM), as used herein, refers to any material generated by removing mineral material from bone tissue. In some embodiments, the DBM compositions as used herein include preparations containing less than 5% calcium and, in some embodiments, less than 1% calcium by weight. In some embodiments, the DBM compositions include preparations that contain less than 5, 4, 3, 2 and/or 1% calcium by weight. In other embodiments, the DBM compositions comprise partially demineralized bone (for example, preparations with greater than 5% calcium by weight but containing less than 100% of the original starting amount of calcium).

Osteoconductive, as used herein, refers to the ability of a substance to serve as a template or substance along which bone may grow.

Osteogenic, as used herein, refers to materials containing living cells capable of differentiation into bone tissue.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," Clinical Orthopaedics & Rel. Res., 357:219-228, December 1998, incorporated herein by reference.

Superficially demineralized, as used herein, refers to bone-derived elements possessing at least about 90 weight percent of their original inorganic mineral content. In some embodiments, superficially demineralized contains at least about 90, 91, 92, 93, 94, 95, 96, 97, 98 and/or 99 weight percent of their original inorganic material. The expression "fully demineralized" as used herein refers to bone containing less than 8% of its original mineral context. In some embodiments, fully demineralized contains about less than 8, 7, 6, 5, 4, 3, 2 and/or 1% of its original mineral content.

The expression "average length to average thickness ratio" as applied to the DBM fibers of the present application means the ratio of the longest average dimension of the fiber (average length) to its shortest average dimension (average thickness). This is also referred to as the "aspect ratio" of the fiber.

Fibrous, as used herein, refers to bone elements whose average length to average thickness ratio or aspect ratio of the fiber is from about 50:1 to about 1000:1. In some embodiments, average length to average thickness ratio or aspect ratio of the fiber is from about 50:1, 75:1, 100:1, 125:1, 150:1, 175:1, 200:1, 225:1, 250:1, 275:1, 300:1, 325:1, 350:1, 375:1, 400:1, 425:1, 450:1, 475:1, 500:1, 525:1, 550:1, 575:1, 600:1, 625:1, 650:1, 675:1, 700:1, 725:1, 750:1, 775:1, 800:1, 825:1, 850:1, 875:1, 900:1, 925:1, 950:1, 975:1 and/or 1000:1. In overall appearance, the fibrous bone elements can be described as bone fibers, threads, narrow strips, or thin sheets. Often, where thin sheets are produced, their edges tend to curl up toward each other. The fibrous bone elements can be substantially linear in appearance or they can be coiled to resemble springs. In some embodiments, the bone fibers are of irregular shapes including, for example, linear, serpentine or curved shapes. The bone fibers are demineralized, however some of the original mineral content may be retained when desirable for a particular embodiment. In various embodiments, the bone fibers are mineralized. In some embodiments, the fibers are a combination of demineralized and mineralized.

Non-fibrous, as used herein, refers to elements that have an average width substantially larger than the average thickness of the fibrous bone element or aspect ratio of less than from about 50:1 to about 1000:1. The non-fibrous bone elements are shaped in a substantially regular manner or specific configuration, for example, triangular prism, sphere, cube, cylinder and other regular shapes. By contrast, particles such as chips, shards, or powders possess irregular or random geometries. It should be understood that some variation in dimension will occur in the production of the elements of this application and elements demonstrating such variability in dimension are within the scope of this application and are intended to be understood herein as being within the boundaries established by the expressions "mostly irregular" and "mostly regular."

The bone material can have a bioactive agent mixed with it. Bioactive agent or bioactive compound is used herein to refer to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, antidepressants, anti-psychotic substances, anti-emetics, and imaging agents. In certain embodiments, the bioactive agent is a drug. Bioactive agents further include RNAs, such as siRNA, and osteoclast stimulating factors. In some embodiments, the bioactive agent may be a factor that stops, removes, or reduces the activity of bone growth inhibitors. In some embodiments, the bioactive agent is a growth factor, cytokine, extracellular matrix molecule or a fragment or derivative thereof, for example, a cell attachment sequence such as RGD. A more complete listing of bioactive agents and specific drugs suitable for use in the present application may be found in Pharmaceutical Substances: Syntheses, Patents, Applications by Axel Kleemann and Jurgen Engel, Thieme Medical Publishing, 1999; Merck Index: An Encyclopedia of Chemicals, Drugs, and Biologicals, edited by Susan Budavari et al., CRC Press, 1996; and United States Pharmacopeia-25/National Formulary-20, published by the United States Pharmacopeia Convention, Inc., Rockville Md., 2001, each of which is incorporated herein by reference. In some embodiments, bioactive agents include nutrients, oxygen sources, and hypoxic inducers such as carbon monoxide or iron chelators.

Percutaneous, as used herein, refers to a surgical method where entry to the spine is by puncture or minor incision, of instrumentation through the skin or mucous membrane and/or any other body layers necessary to reach the site of the procedure.

The devices, bone materials, kits and methods may be employed to treat spinal disorders such as, for example, degenerative disc disease, disc herniation, osteoporosis, spondylolisthesis, stenosis, scoliosis and other curvature abnormalities, kyphosis, tumors and fractures. The devices, bone materials, kits and methods may be employed with other osteal and bone related applications, including those associated with diagnostics and therapeutics. They may also be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The devices, bone materials, kits and methods may also be alternatively employed with procedures for treating the lumbar, cervical, thoracic, sacral and pelvic regions of a spinal column. They may also be used on animals, bone models and other non-living substrates, such as, for example, in training, testing and demonstration.

In various embodiments, the bone material comprises poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, L-lactide-co-ε-caprolactone or a combination thereof.

In some embodiments, the devices, bone materials, kits and methods are used in minimally invasive surgeries and the bone material is percutaneously delivered to a surgical site or the surgical site is the posterior spine.

Devices

Referring to FIGS. 1 to 10, a device 20 is provided for mixing and dispensing bone material 22 (e.g., bone graft). The mixing and dispensing of bone material can occur in a single device. Liquid and solid (e.g., particulates) components are mixed within the interior surface of the device to form a mixed bone material. In some embodiments, the bone material can be dry bone material and preloaded in the device by the manufacturer or it can be loaded during the surgical procedure. In some embodiments, the device can be a syringe.

Figure 2:
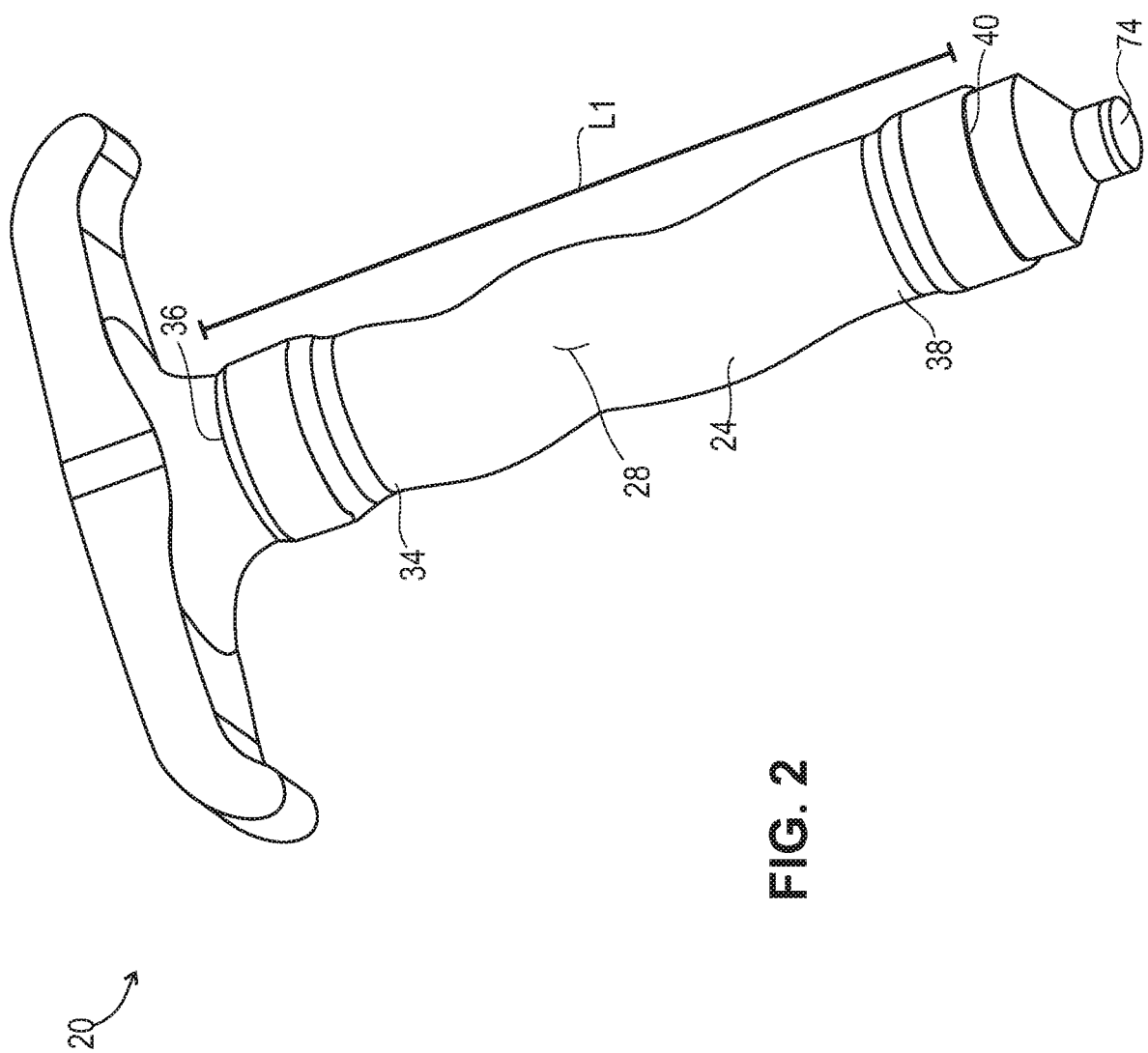
FIG. 2 is a perspective view of the device of FIG. 1. In this embodiment, the device is shown without the plunger.
Figure 3:
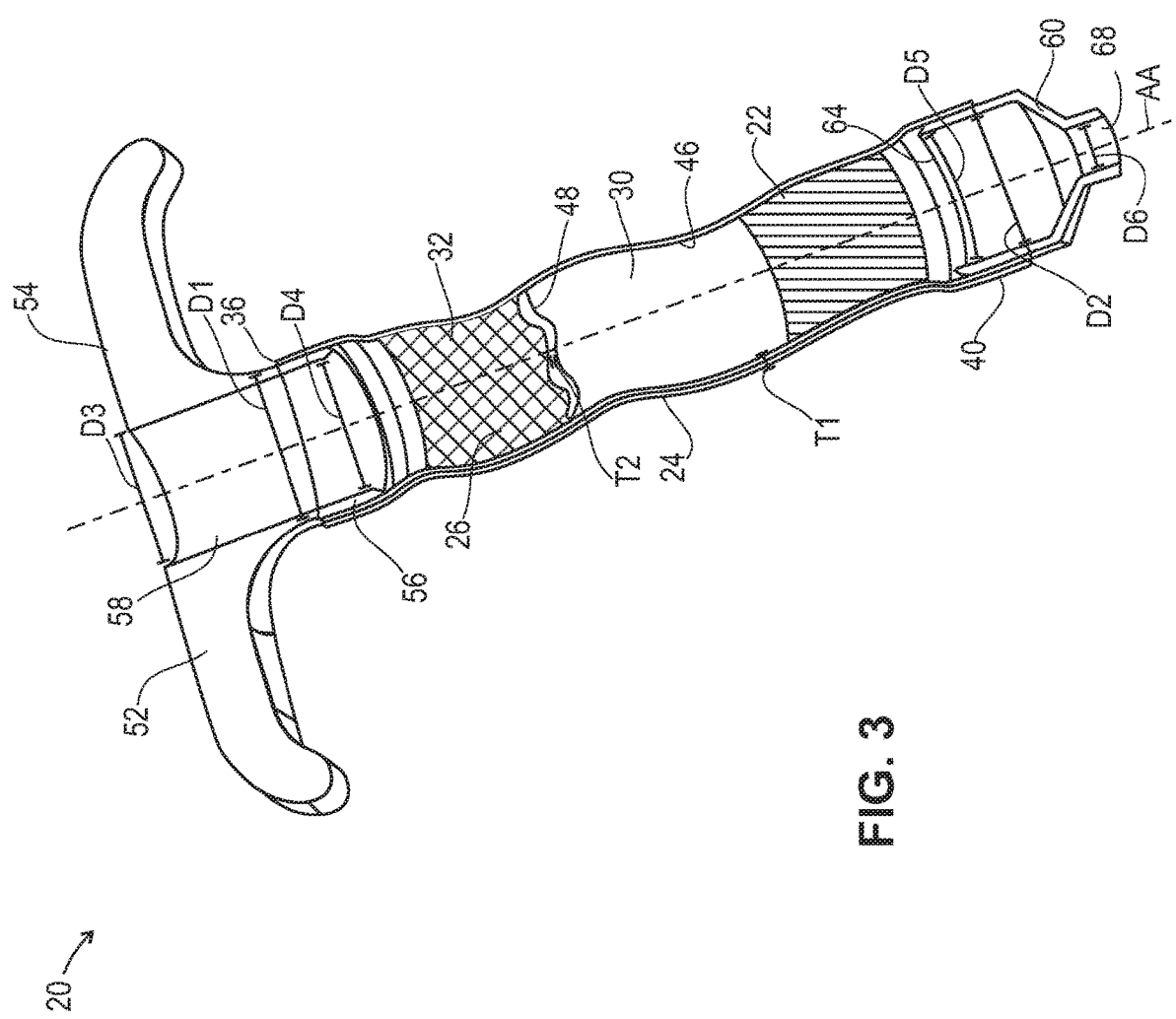
FIG. 3 is a perspective cross sectional view of the device of FIG. 1. In this embodiment, the device is shown without the plunger and includes a frangible barrier defined by the interior surface of the tubular member. The plunger is configured to break the frangible barrier or the frangible barrier can be broken by hand by the user by kneading or manipulating the flexible tubular member to release the fluid into the bone material. In the embodiment shown, the frangible barrier separates the fluid from the particulate bone material. In the embodiment shown, the tubular member is shown kneaded to aid in mixing.
Figure 3A:
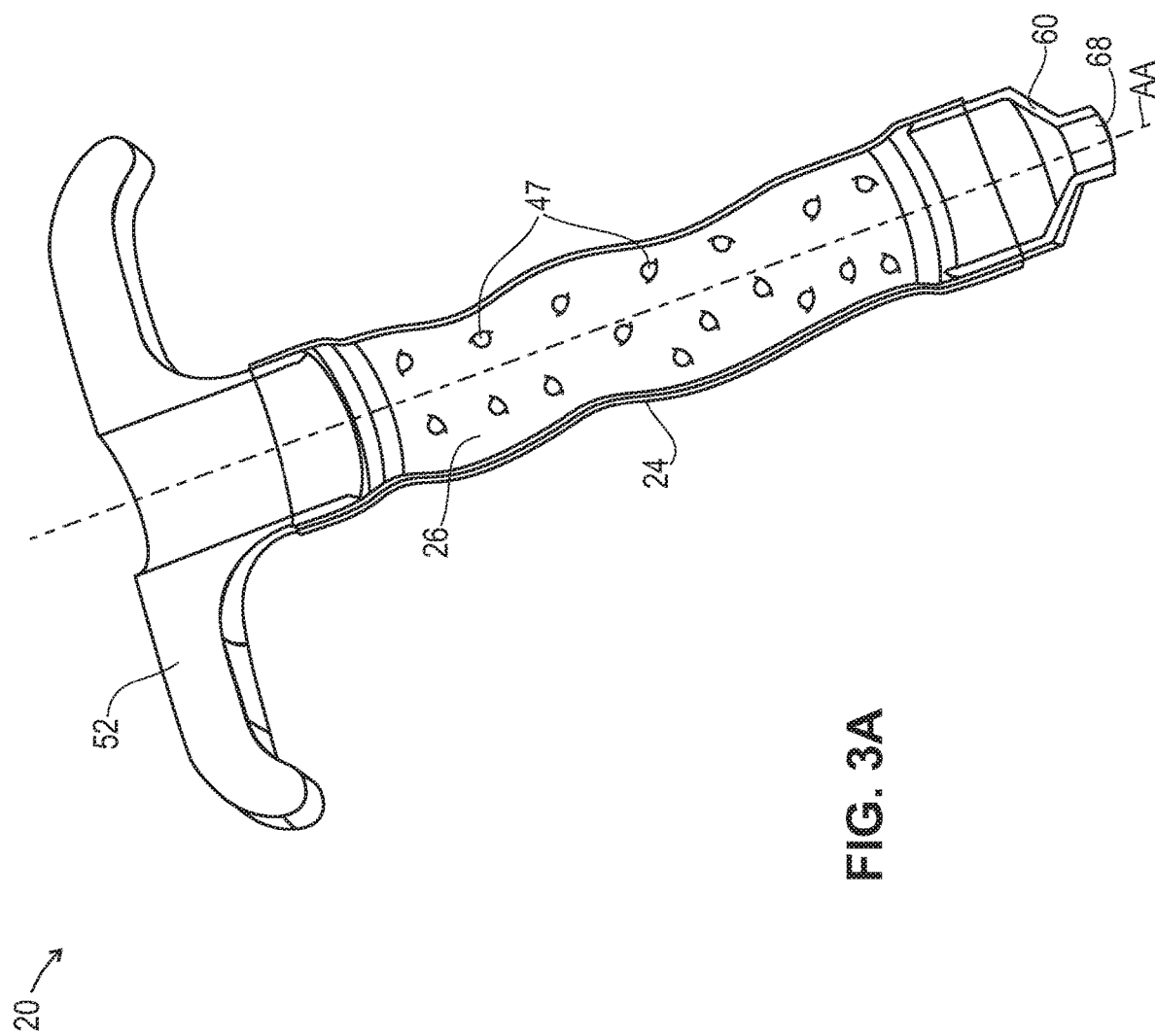
FIG. 3A is a perspective cross sectional view of the device of FIG. 1. In this embodiment, an interior surface of the tubular member can include interior textures or raised surfaces, such as bumps to increase the user's ability to mix the bone material and the fluid.
Figure 3B:
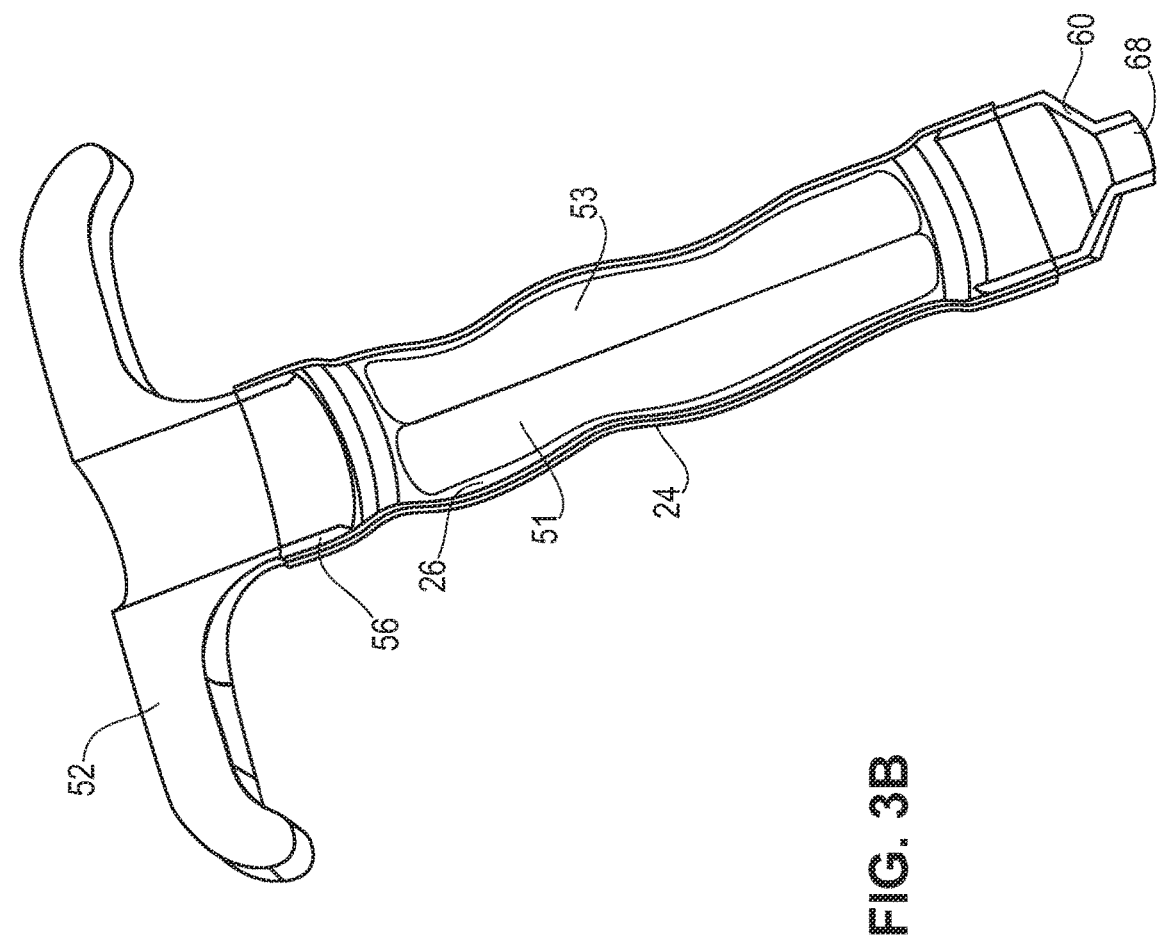
FIG. 3B is a perspective cross sectional view of the device of FIG. 1. In this embodiment, a frangible barrier is positioned vertically within the tubular member such that sealed compartments within the tubular member are formed. The frangible barrier defines a first compartment and a second compartment within the interior surface of the tubular member.
Figure 3C:
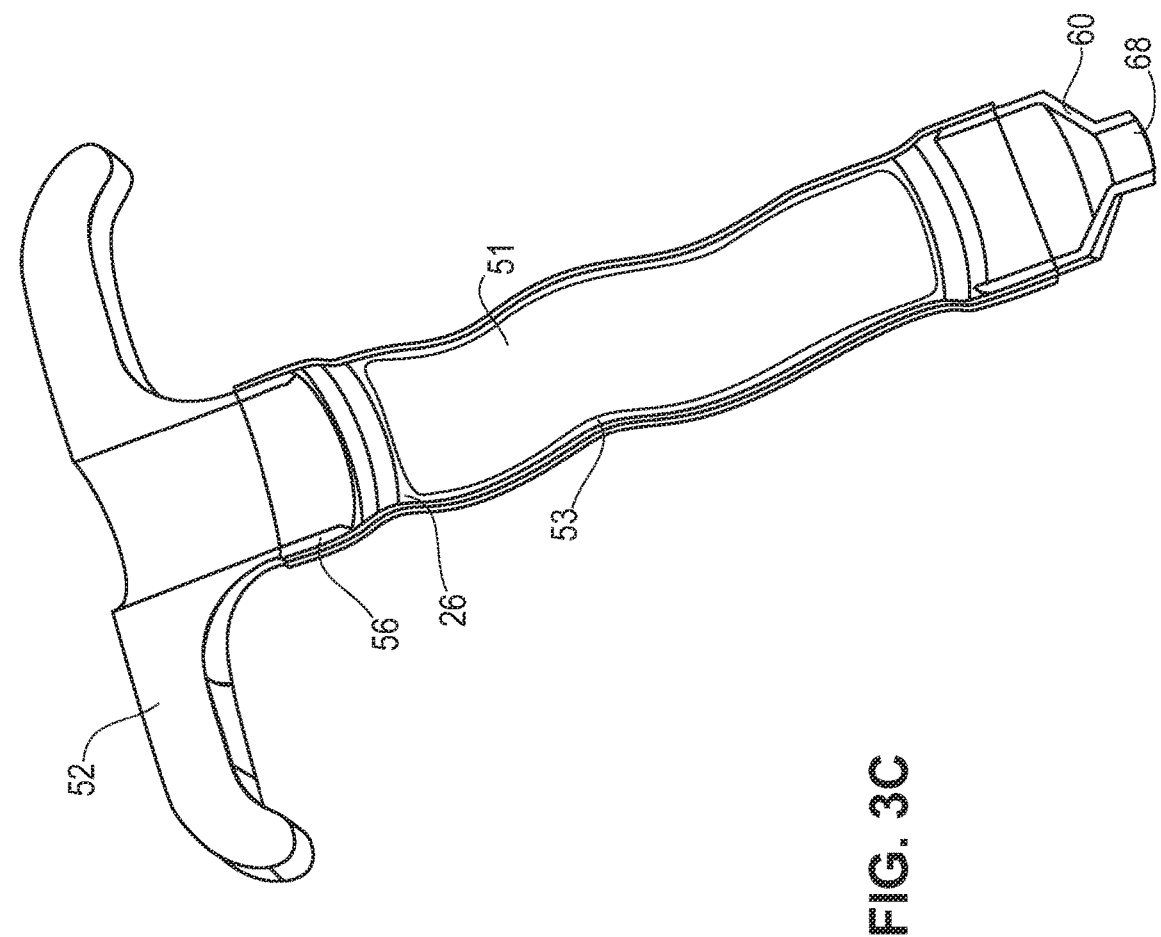
FIG. 3C is a perspective cross sectional view of the device of FIG. 1. In this embodiment, a frangible barrier is positioned vertically within the tubular member such that a tube within a tube configuration is formed. The first compartment is an inner compartment and the second compartment is an outer compartment. Fluid and/or bone material can be separately disposed within each compartment.
Figure 3D:
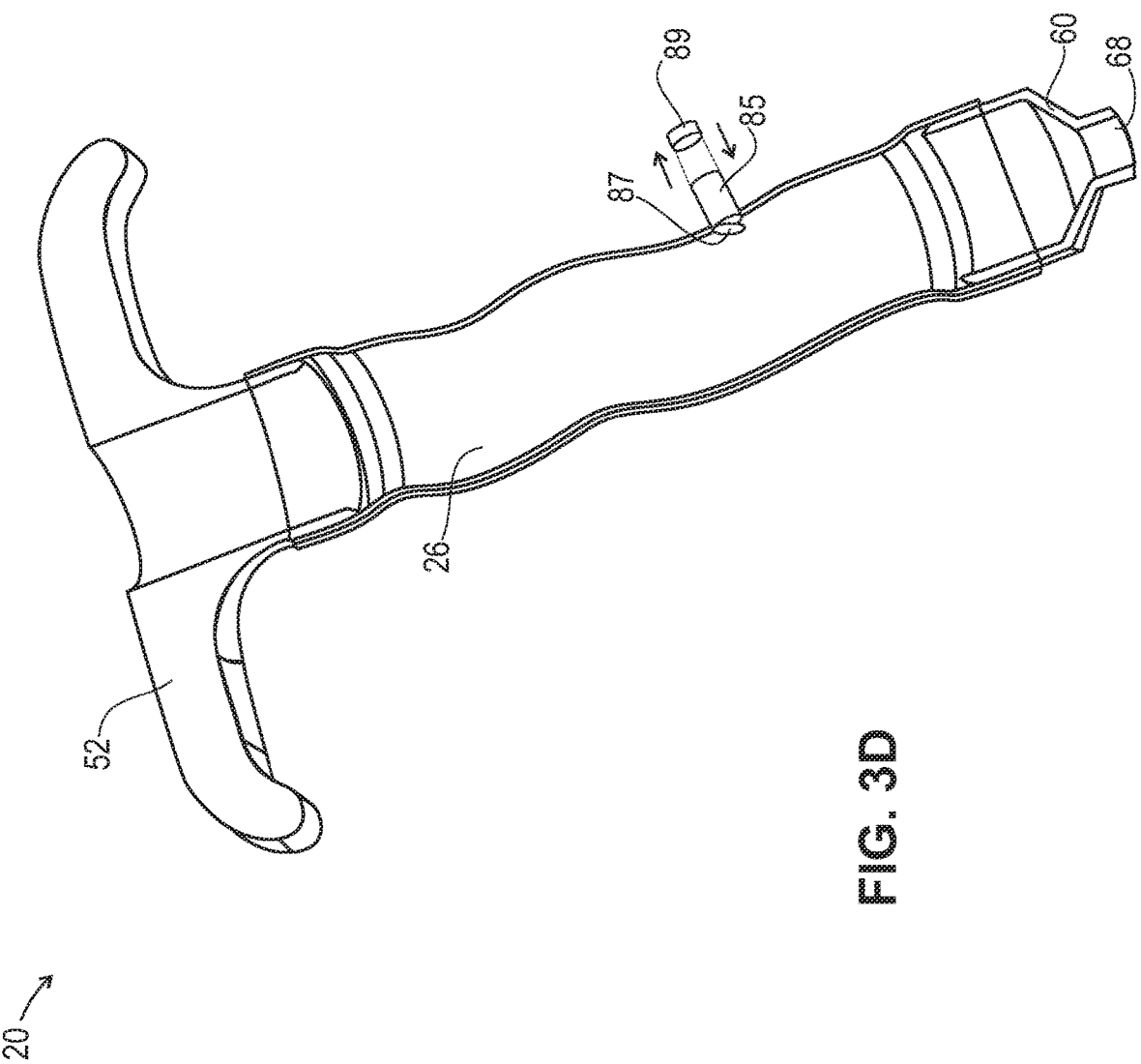
FIG. 3D is a perspective cross sectional view of the device of FIG. 1. In this embodiment, fluid can be introduced through an opening in a nozzle of the device or through a port disposed on the tubular member. The port includes a one-way valve that only allows fluid into the tubular member and the port can be closed via a cap.
Figure 4:
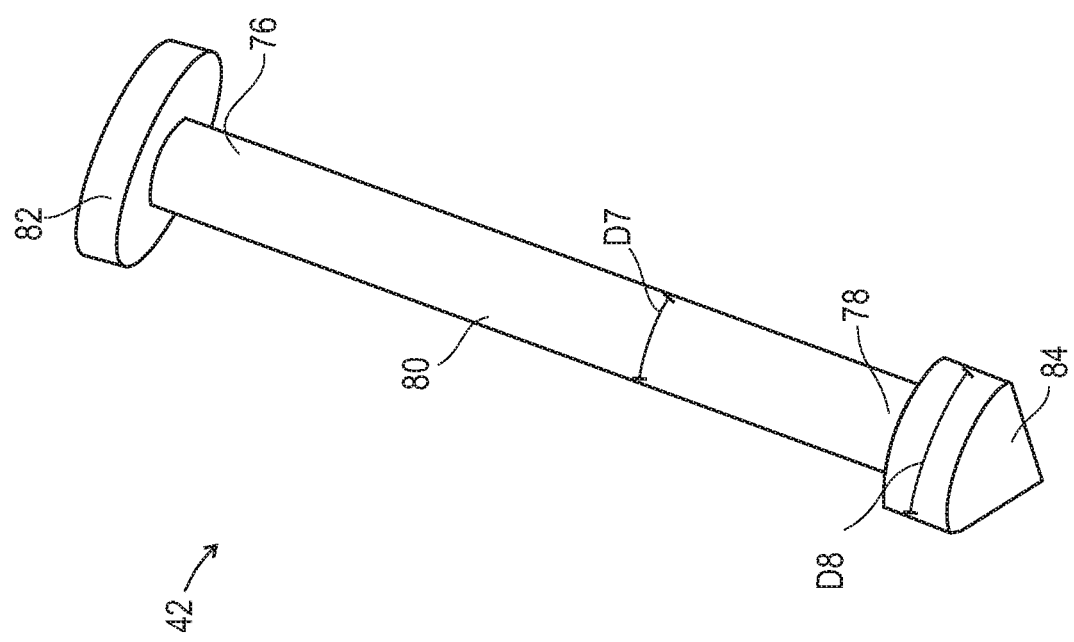
FIG. 4 is a perspective view of the plunger of the device of FIG. 1.

The device includes a flexible tubular member 24 having an interior surface 26 and an exterior surface 28, as shown in FIGS. 2-3D. In some embodiments, the tubular member is a syringe barrel or a bottle. The interior surface defines a mixing space or a channel 30 configured to receive the bone material and a fluid 32. In some embodiments, the mixing space can be a gap to allow mixing of fluid and the bone material. The bone material and the fluid can be mixed and disposed within the channel of the tubular member. The user can mix the bone material and the fluid by kneading the tubular member of the syringe. In some embodiments, the tubular member can be kneaded by the user's palm and fingers or by squeezing the tubular member. In some embodiments, the interior surface and the exterior surface of the tubular member are not porous such that the bone material does not diffuse out of the tubular member. In some embodiments, the interior and the exterior surface are both kneadable. In some embodiments, opening 68 can receive a cap 74 to prevent spilling of the bone material during mixing, as later described.

The tubular member comprises a proximal end 34 defining a proximal opening 36, a distal end 38 defining a distal opening 40 and a longitudinal axis AA disposed therebetween. The proximal opening is configured to slidably receive a plunger 42, and the distal opening is configured to dispense a mixed bone material 44 (e.g., a combination of the bone material and the fluid) from the interior surface of the tubular member, as described herein. The proximal opening has a diameter D1 and the distal opening has a diameter D2, as shown in FIG. 3. In some embodiments, diameters D1 and D2 can be the same size, D1 can be greater than D2 or D2 can be greater than D1. In some embodiments, D1 and D2 can be from about 4 mm to about 30 mm, from about 4 mm to about 20 mm, from about 4 mm to about 10 mm, from about 10 mm to about 30 mm, from about 10 mm to about 20 mm, from about 10 to about 15 mm, from about 15 mm to about 30 mm, from about 15 to about 25 mm, from about 15 mm to about 20 mm, from about 20 mm to about 30 mm or from about 20 mm to about 25 mm. In some embodiments, diameters D1 and D2 can be from about 4, 5, 6, 7, 8, 9, 10, 11, 12, 13, 14, 15, 16, 17, 18, 19, 20, 21, 22, 23, 24, 25, 26, 27, 28, 29 to about 30 mm.

The tubular member can have a length L1, as shown in FIG. 2. The length L1 can be from about 1 inch to about 20 inches, from about 1 to about 15 inches, from about 1 to about 10 inches, from about 1 to about 5 inches, from about 5 to about 20 inches, from about 5 to about 15 inches, from about 5 to about 10 inches, from about 10 to about 20 inches, from about 10 to about 15 inches, or from about 15 to about 20 inches. In some embodiments, the length L1 can be from about 1, 2, 3, 4, 5, 6, 7, 8, 9, 10, 11, 12, 13, 14, 15, 16, 17, 18, 19 to about 20 inches.

In some embodiments, the tubular member can have a certain wall 46 thickness T1, as shown in FIG. 3. The wall thickness T1 can be defined by the interior and exterior surfaces. In some embodiments, the wall thickness T1 can be about 1 mm to about 10 mm, from about 1 mm to about 8 mm, from about 1 mm to about 6 mm, from about 1 mm to about 4 mm, from about 1 mm to about 2 mm, from about 2 mm to about 10 mm, from about 2 mm to about 8 mm, from about 2 mm to about 6 mm, from about 2 mm to about 4 mm, from about 4 mm to about 10 mm, from about 4 mm to about 8 mm, from about 4 mm to about 6 mm, from about 6 mm to about 10 mm, from about 6 mm to about 8 mm, or from about 8 mm to about 10 mm. In some embodiments, the wall thickness of the tubular member can be from about 1, 2, 3, 4, 5, 6, 7, 8, 9 to about 10 mm.

In some embodiments, the interior surface of the tubular member can include interior textures or raised surfaces, such as bumps 47 to increase the user's ability to mix the bone material and the fluid, as shown in FIG. 3A. In some embodiments, the interior textures or raised surfaces, can also include, but are not limited ridges.

Figure 2A:
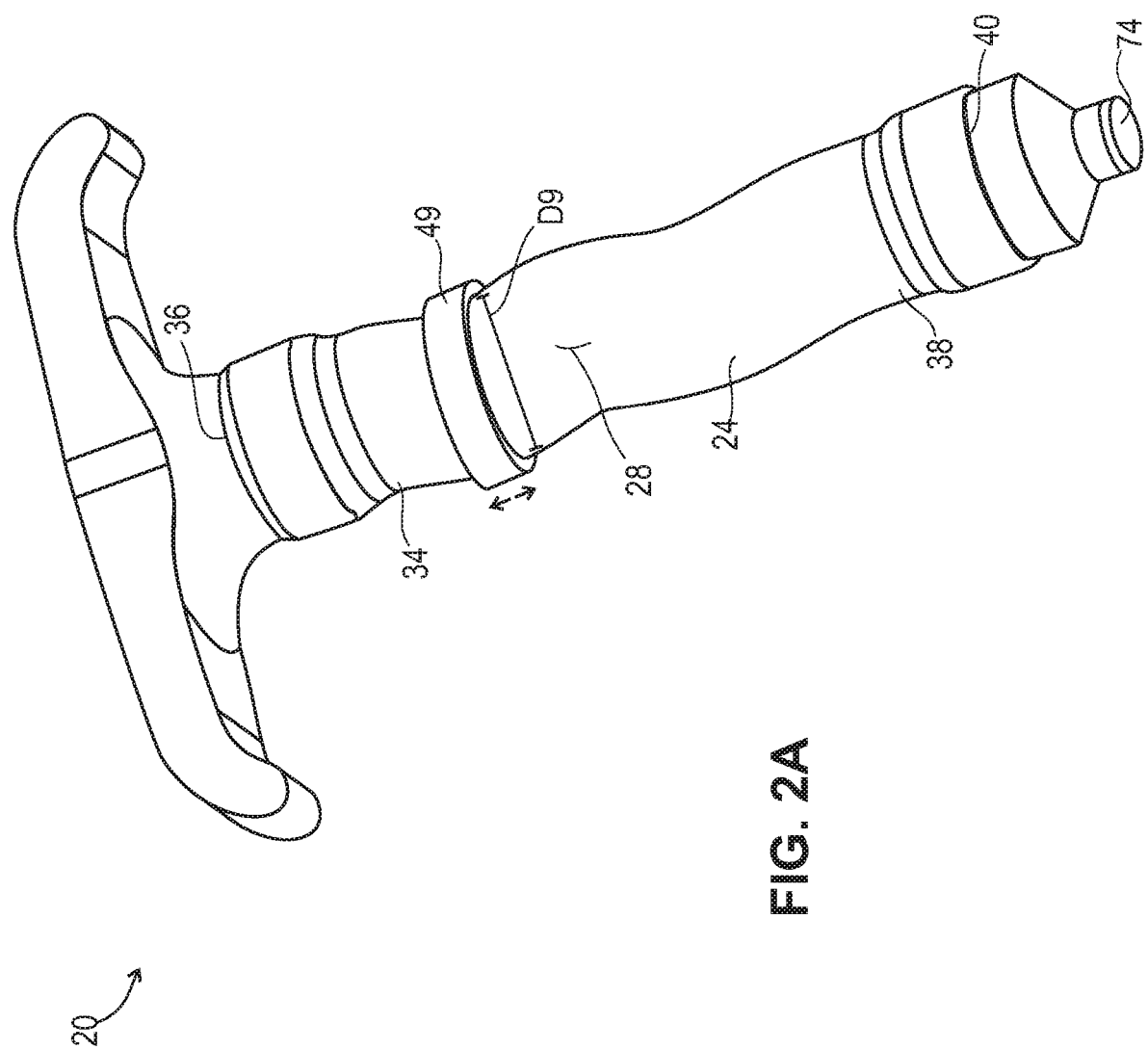
FIG. 2A is a perspective view of the device of FIG. 1. In this embodiment, the device is shown with a ring that movably engages with the exterior surface of the tubular member to facilitate mixing of the bone material and the fluid located within the interior surface of the tubular member.

In some embodiments, as shown in FIG. 2A, a ring 49 can movably engage with the exterior surface of the tubular member to facilitate mixing of the bone material and the fluid located within the interior surface of the tubular member. In this embodiment, as the ring is moved up and down across the exterior surface of the tubular member, as shown by the arrows, the bone material and the fluid are mixed without the need for the user's hands alone. In some embodiments, the ring can be rigid or flexible. The ring has a diameter D9. In some embodiments, D9 can be from about 4 mm to about 32 mm, from about 4 mm to about 20 mm, from about 4 mm to about 10 mm, from about 10 mm to about 32 mm, from about 10 mm to about 20 mm, from about 10 to about 15 mm, from about 15 mm to about 32 mm, from about 15 to about 25 mm, from about 15 mm to about 20 mm, from about 20 mm to about 32 mm or from about 20 mm to about 25 mm. In some embodiments, diameter D9 can be from about 4, 5, 6, 7, 8, 9, 10, 11, 12, 13, 14, 15, 16, 17, 18, 19, 20, 21, 22, 23, 24, 25, 26, 27, 28, 29, 30, 31 to about 32 mm.

In some embodiments, the tubular member can include a frangible barrier 48 defined by the interior surface, as shown in FIG. 3. The frangible barrier can separate the fluid from the particulate bone material. It will be understood that the fluid can be disposed above or below the frangible barrier and that the bone material can be disposed above or below the frangible barrier. The frangible barrier is configured to break and allow mixing of the fluid with the bone material to create a mixed bone material. The frangible barrier can be broken by a plunger slidably received in the interior surface or by hand during kneading of the tubular member. The device can also be shaken to aid in mixing the fluid with the bone material after the frangible barrier is broken. In some embodiments, the frangible barrier is monolithic with the interior surface. In some embodiments, the frangible barrier is not monolithic with the interior surface. The frangible barrier can be made from the same or a different material as the interior surface. In some embodiments, the frangible barrier can be made from a flexible material but is fixed at a selected position in the interior surface of the tubular member.

In some embodiments, compartments can be made from a frangible material and can be positioned vertically within the tubular member, as shown in FIGS. 3B and 3C such that a tube within a tube and/or sealed adjacent compartments within the tubular member are formed. In some embodiments, the frangible material defines a first compartment 51 and a second compartment 53 within the interior surface of the tubular member, as shown in FIG. 3B. In some embodiments, the bone material can be disposed in the first compartment and the fluid can be disposed in the second compartment. In some embodiments, the bone material can be disposed in the second compartment and the fluid can be disposed in the first compartment.

In some embodiments, the first compartment 51 is an inner compartment and the second compartment 53 is an outer compartment, as shown in FIG. 3C. In some embodiments, the fluid can be inserted into the outer or inner compartment, and then the frangible material of the outer or inner compartment where the fluid is inserted into can be broken. In some embodiments, a vacuum can be created via the bone material such that when the frangible material is broken, the fluid will combine with the bone material.

In some embodiments, the frangible barrier 48 of FIG. 3 has a thickness T2. The thickness T2 can be from about 1 mm to about 4 mm or from about 2 mm to about 4 mm. In some embodiments, the thickness T2 can be from about 1, 2, 3 to about 4 mm. In some embodiments, the frangible barrier can be rigid or flexible. In some embodiments, the tubular member is less flexible than the frangible barrier. It is to be understood that the frangible material that defines first compartment 51 and second compartment 53 of FIGS. 3B and 3C can have the same or a different thickness than thickness T2 of frangible barrier 48.

In some embodiments, the frangible barrier can be disposed in any location within the interior surface. In some embodiments, the frangible barrier can be adjacent to the proximal end of the tubular member, adjacent the distal end of the tubular member and/or in the center of the interior surface of the tubular member. In some embodiments, the tubular member can include one or more frangible barriers, for example, 1, 2, 3, 4, 5, 6 or more frangible barriers. In some embodiments, the one or more frangible barriers can have the same or different bone material(s) disposed in between the frangible barriers and/or can have one or more of the same of different fluids disposed in between the frangible barriers. In some embodiments, the frangible barrier can be parallel or perpendicular relative to axis AA. In some embodiments, the frangible barrier can have perforations or score lines on a portion of a surface of the barrier to assist in breaking the frangible barrier. In some embodiments, the device can be a bi-lumen syringe comprising the frangible barrier that separates and breaks to mix.

Figure 5:
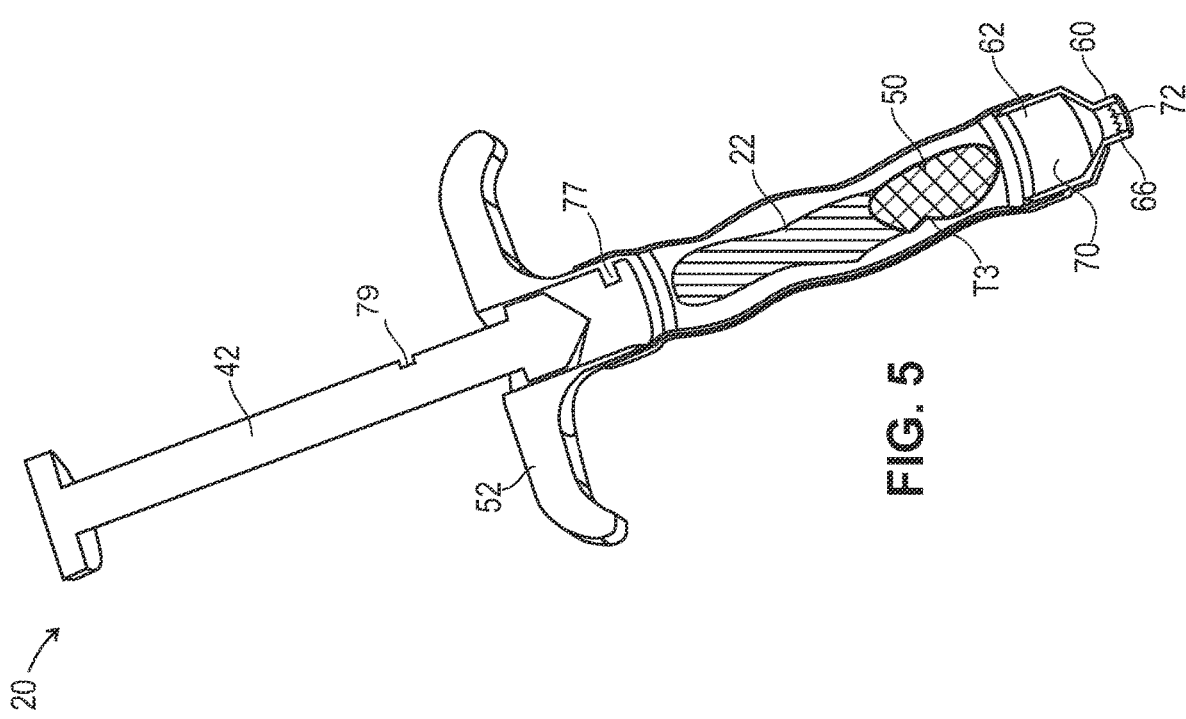
FIG. 5 is a perspective cross sectional view of the device of FIG. 1 preloaded with bone material. In this embodiment, the fluid is disposed in a frangible capsule within the tubular member. A user can knead the tubular member and the frangible capsule will break, causing the fluid to mix with the bone material.
Figure 8:
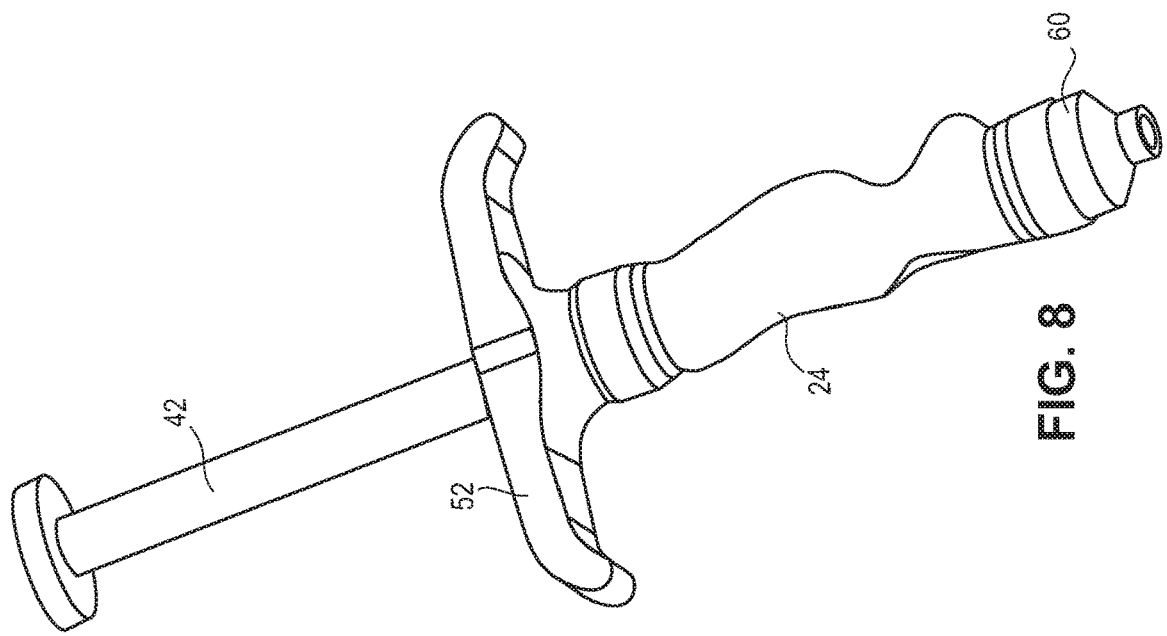
FIG. 8 is a perspective view of the device of FIG. 7 after it has been kneaded. The plunger slides for dispensing causing the tubular member to start to straighten as the mixing space (e.g. the channel) is reloaded.
Figure 7:
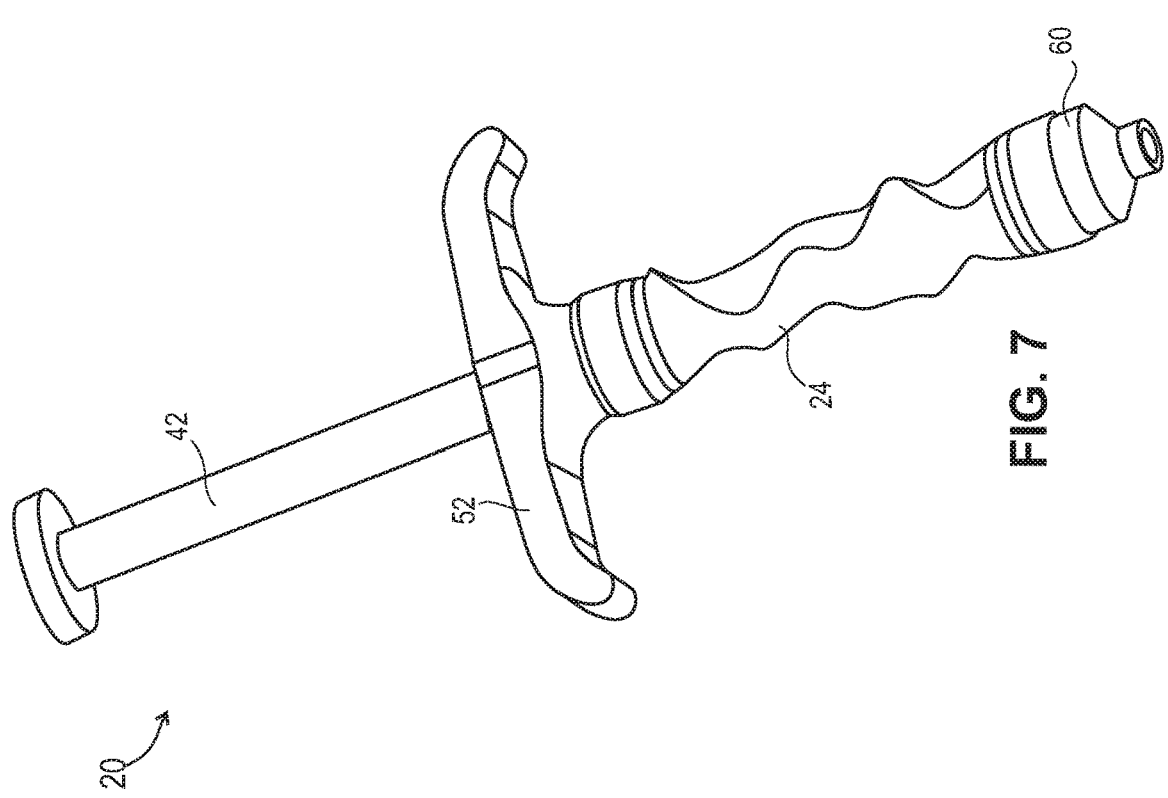
FIG. 7 is a perspective view of the device of FIG. 1 shown in a kneadable configuration.
Figure 9:
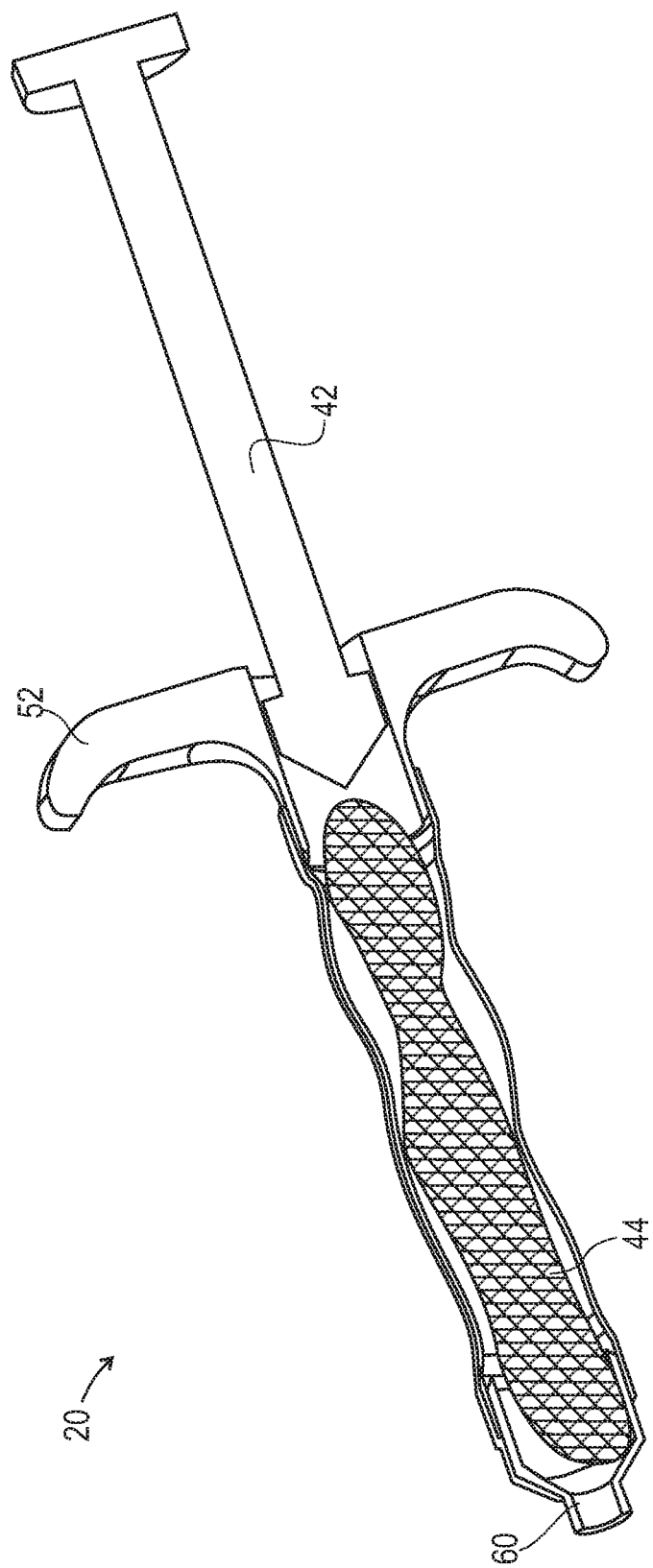
FIG. 9 is a perspective cross sectional view of the device of FIG. 1. In this embodiment, the bone material and fluid have been mixed and are now ready to be dispensed out of the distal opening of the tubular member.

In some embodiments, the fluid is disposed in a frangible capsule 50 that is placed into the tubular member, as shown in FIG. 5. In this embodiment, a user can knead the tubular member and the frangible capsule will break, causing the fluid to mix with the bone material disposed within the channel of the tubular member. In some embodiments, the bone material can be disposed in the frangible capsule and the fluid can be disposed within the channel of the tubular member. In some embodiments, the frangible capsule is made from a material or materials that have a certain thickness T3. In some embodiments, the thickness T3 can be uniform or non-uniform throughout the frangible capsule. In some embodiments, the thickness is from about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9 to about 4 mm. In some embodiments, the size of the frangible capsule can be from about 0.6 to about 5 mm. In some embodiments, the size of the frangible capsule can be from about 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 to about 5 mm. In some embodiments, the frangible capsule can be made from a biodegradable material such as, for example, gelatin.

In some embodiments, the device may include one or more frangible capsules that are placed within the tubular member by the manufacturer or at the time of surgery. In some embodiments, one or more frangible capsules can include from about 1, 2, 3, 4, 5, 6, 7, 8, 9, 10, 11, 12, 13, 14, 15, 16, 17, 18, 19 to about 20 frangible capsules. In some embodiments, the frangible capsules are permeable, semi-permeable or non-permeable.

In some embodiments, the one or more frangible capsules can be attached to the plunger instead of being placed within the tubular member by the manufacturer. In some embodiments, when the one or more frangible capsules are attached to a tip of the plunger, the one or more frangible capsules will break when the plunger is driven distally into the bone material disposed within the channel of the tubular member. In some embodiments, the one or more frangible capsules can be contained within the plunger, and then broken by a separate plunger within the plunger (not shown), such that the separate plunger breaks the one or more frangible capsules within the tubular member without moving plunger 42.

In some embodiments, the proximal end of the tubular member includes a handle 52. In some embodiments, the handle is rigid and is less flexible than the tubular member. In some embodiments, the handle is a T-shaped handle that fixedly engages with the proximal end of the tubular member. In some embodiments, engagement can include, but is not limited to, threaded engagement, adhesive engagement, melting or fusing, staking, or friction fit engagement. In some embodiments, the handle is monolithic to the tubular member.

The handle includes a proximal end 54, a distal end 56, and an opening or bore 58 that is centrally disposed in the handle, as shown in FIG. 3. Longitudinal axis AA runs through the opening, and the opening is configured to slidably receive the plunger. The opening is in alignment with the proximal opening of the tubular member. The opening has diameters D3 and D4, as shown in FIG. 3. In some embodiments, diameters D1, D2, D3 and D4 can be the same size or different sizes. In some embodiments, diameters D3 and D4 can be from about 4 mm to about 30 mm, from about 4 mm to about 20 mm, from about 4 mm to about 10 mm, from about 10 mm to about 30 mm, from about 10 mm to about 20 mm, from about 10 to about 15 mm, from about 15 mm to about 30 mm, from about 15 to about 25 mm, from about 15 mm to about 20 mm, from about 20 mm to about 30 mm or from about 20 mm to about 25 mm. In some embodiments, diameters D3 and D4 can be from about 4, 5, 6, 7, 8, 9, 10, 11, 12, 13, 14, 15, 16, 17, 18, 19, 20, 21, 22, 23, 24, 25, 26, 27, 28, 29 to about 30 mm.

The distal end of the tubular member includes a nozzle 60 that is configured to dispense the mixed bone material. In some embodiments, the nozzle is rigid and is less flexible than the tubular member. In some embodiments, the nozzle fixedly engages with the distal end of the tubular member. In some embodiments, engagement can include, but is not limited to, threaded engagement, adhesive engagement, or friction fit engagement. In some embodiments, the nozzle is monolithic to the tubular member.

The nozzle includes a proximal end 62 having an opening 64, and a distal end 66 having an opening 68, as shown in FIGS. 3 and 5. Longitudinal axis AA runs through the nozzle. The openings of the nozzle are in alignment with the distal opening of the tubular member. The openings have diameters D5 and D6, as shown in FIG. 3. In some embodiments, diameters D1, D2, D3, D4 and D5 can be the same size or different sizes. In some embodiments, diameter D5 is greater than diameter D6 when the nozzle is in a tapered configuration, or diameter D5 and D6 can be the same size. In some embodiments, diameter D5 can be from about 4 mm to about 30 mm, from about 4 mm to about 20 mm, from about 4 mm to about 10 mm, from about 10 mm to about 30 mm, from about 10 mm to about 20 mm, from about 10 to about 15 mm, from about 15 mm to about 30 mm, from about 15 to about 25 mm, from about 15 mm to about 20 mm, from about 20 mm to about 30 mm or from about 20 mm to about 25 mm. In some embodiments, diameter D5 can be from about 4, 5, 6, 7, 8, 9, 10, 11, 12, 13, 14, 15, 16, 17, 18, 19, 20, 21, 22, 23, 24, 25, 26, 27, 28, 29 to about 30 mm. In some embodiments, diameter D6 can be from about 2 mm to about 30 mm, from about 2 mm to about 20 mm, from about 2 mm to about 10 mm, from about 4 mm to about 30 mm, from about 4 mm to about 20 mm, from about 4 mm to about 10 mm, from about 10 mm to about 30 mm, from about 10 mm to about 20 mm, from about 10 to about 15 mm, from about 15 mm to about 30 mm, from about 15 to about 25 mm, from about 15 mm to about 20 mm, from about 20 mm to about 30 mm or from about 20 mm to about 25 mm. In some embodiments, diameter D6 can be from about 2, 3, 4, 5, 6, 7, 8, 9, 10, 11, 12, 13, 14, 15, 16, 17, 18, 19, 20, 21, 22, 23, 24, 25, 26, 27, 28, 29 to about 30 mm.

The nozzle has an interior surface 70, and in some embodiments, the interior surface comprises at least one projection, such as blades 72 for mixing and/or dispensing the mixed bone material, as shown in FIG. 5. In some embodiments, the blades can be twisted so that the bone material can be mixed. In some embodiments, the blades can be at the distal end of the nozzle. In some embodiments, the nozzle can include 1, 2, 3, 4, 5, 6, 7, 8, 9, 10 or more projections or blades. In some embodiments, the nozzle can be made from metal, plastic, rubber or a combination thereof.

In some embodiments, where there is no frangible barrier, the tubular member can have the bone material disposed within the interior surface. The user angles the tubular member to prevent spillage of the bone material from the distal opening. The user by pulling the plunger in the proximal direction draws fluid into the interior surface to mix with the bone material. The user can then cap the distal opening and the tubular member can be kneaded to aid in mixing. The cap can be removed and depressing the plunger toward the distal opening dispenses the mixed bone material.

In some embodiments, the distal end of the nozzle is configured to receive the cap to hold the mixed bone material within the interior surface of the tubular member, as shown in FIG. 2. In some embodiments, the cap can engage the distal end of the nozzle via friction fit, threaded connection or snap fit engagement.

Figure 2B:
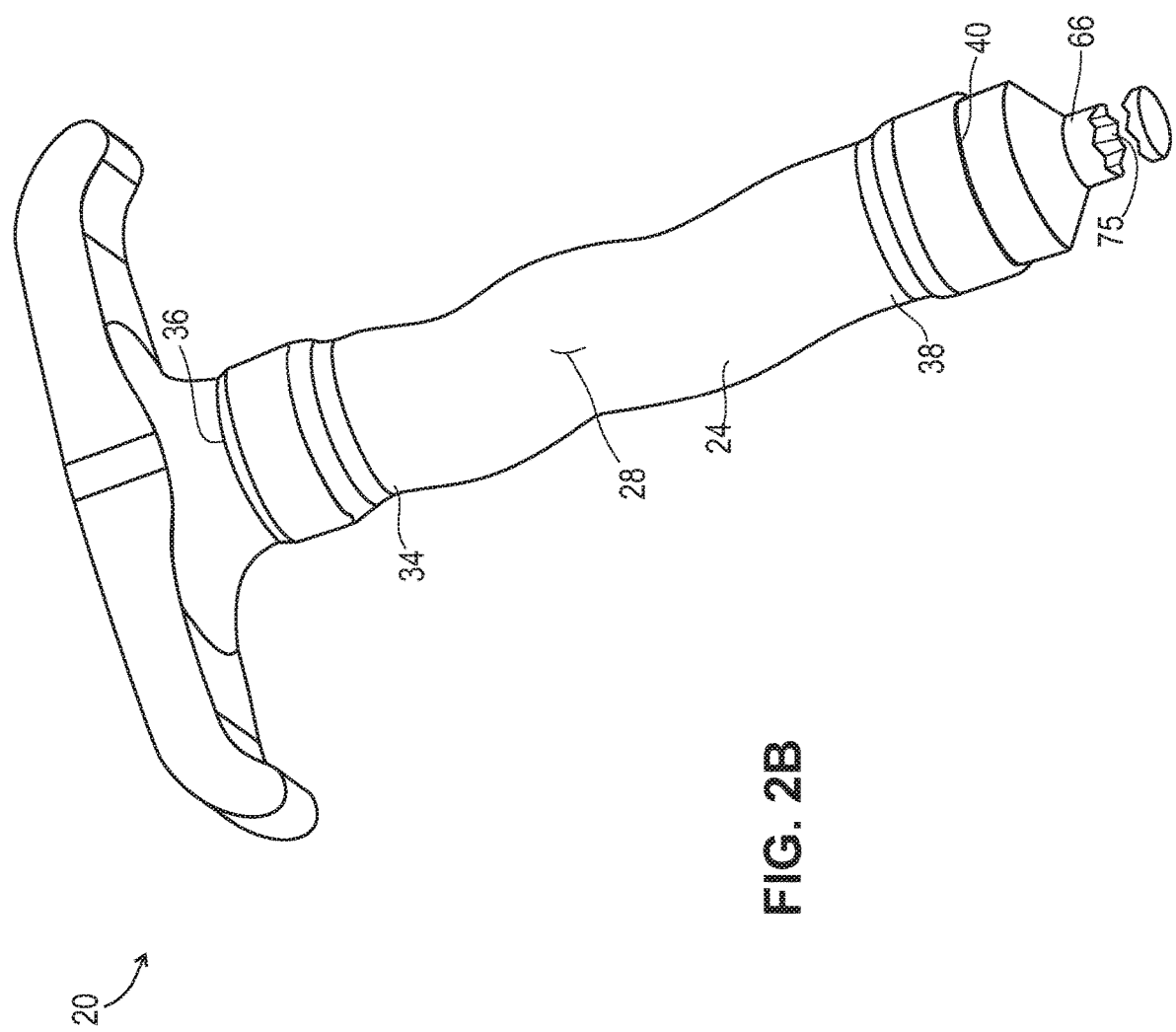
FIG. 2B is a perspective view of the device of FIG. 1. In this embodiment, a nozzle of the device is shown integrally formed with the tubular member and a distal end of the nozzle is solid. Before use and after the bone material and fluid are mixed together, the nozzle can be cut at the distal end to dispense the mixed bone material.

In some embodiments, the nozzle is integrally formed with the tubular member and does not include opening 68, but instead is solid where opening 68 would be positioned. In some embodiments, the nozzle can be angled at the distal end. In some embodiments, before use and after the bone material and fluid are mixed together, the nozzle can be cut 75 at the distal end, as shown in FIG. 2B to dispense the mixed bone material.

The device includes plunger 42, as described above and shown in FIG. 4. The plunger is configured to be slidably received by the opening of the handle, the proximal opening of the tubular member and/or the channel of the tubular member to facilitate dispensing of the mixed bone material. When the plunger engages with the tubular member, a seal is formed between the plunger and the tubular member such that air cannot escape from the proximal opening of the tubular member during dispensing of the mixed bone material. For example, when the plunger is moved in a downward direction toward the distal end of the tubular member, the pressure inside of the tubular member will straighten the syringe, giving it the rigidity of a standard syringe, allowing for the same handling as a normal syringe. The mixed bone material can then be dispensed from the distal end of the nozzle of the device and administered to a surgical site. In some embodiments, a seal is maintained between the plunger and the tubular member during mixing and/or dispensing.

In some embodiments, a detent formed by indent 79 and projection 77 is located between the handle and the plunger, as shown in FIG. 5, such that the plunger can be advanced further through the tubular member to ensure that the correct amount of pressure is applied to the tubular member to make it rigid.

The plunger includes a proximal end 76, a distal end 78, and a body 80 disposed on longitudinal axis AA. In some embodiments, the plunger is rigid and is less flexible than the tubular member. In some embodiments, the proximal end of the plunger includes a gripping portion 82. The gripping portion can be disc shaped, square, spherical, triangular, irregularly shaped and/or can include a textured surface to assist in gripping. In some embodiments, the distal end of the plunger includes a tapered or angled tip 84, that is configured to break the frangible barrier within the interior surface of the tubular member. In some embodiments, the tip is sharp.

In some embodiments, the body of the plunger has a diameter D7 and the widest point of the tip has a diameter D8. In some embodiments, D8 is greater than D7 or D7 is equal to D8. In some embodiments, diameters D1, D2, D3, D4, D5 and D8 can be the same size or different sizes. In some embodiments, diameter D8 can be from about 4 mm to about 30 mm, from about 4 mm to about 20 mm, from about 4 mm to about 10 mm, from about 10 mm to about 30 mm, from about 10 mm to about 20 mm, from about 10 to about 15 mm, from about 15 mm to about 30 mm, from about 15 to about 25 mm, from about 15 mm to about 20 mm, from about 20 mm to about 30 mm or from about 20 mm to about 25 mm. In some embodiments, diameter D8 can be from about 4, 5, 6, 7, 8, 9, 10, 11, 12, 13, 14, 15, 16, 17, 18, 19, 20, 21, 22, 23, 24, 25, 26, 27, 28, 29 to about 30 mm. In some embodiments, diameter D7 can be from about 2 mm to about 30 mm, from about 2 mm to about 20 mm, from about 2 mm to about 10 mm, from about 4 mm to about 30 mm, from about 4 mm to about 20 mm, from about 4 mm to about 10 mm, from about 10 mm to about 30 mm, from about 10 mm to about 20 mm, from about 10 to about 15 mm, from about 15 mm to about 30 mm, from about 15 to about 25 mm, from about 15 mm to about 20 mm, from about 20 mm to about 30 mm or from about 20 mm to about 25 mm. In some embodiments, diameter D7 can be from about 2, 3, 4, 5, 6, 7, 8, 9, 10, 11, 12, 13, 14, 15, 16, 17, 18, 19, 20, 21, 22, 23, 24, 25, 26, 27, 28, 29 to about 30 mm.

In some embodiments, the fluid can be introduced through opening 68 in the nozzle, or through a port 85 that is disposed on the tubular member, as shown in FIG. 3D. The port includes a one-way valve 87 that only allows fluid into the tubular member, as shown by the arrows. In some embodiments, the port can be closed via a cap 89. In some embodiments, the port can be disposed in a portion of the plunger, such as, for example, centrally down the middle of the plunger, or on the handle. In some embodiments, when the port is located on the handle, the fluid is introduced through the handle via the port, and then the plunger is either translated or rotated to block the one-way valve.

As described above, the tubular member is flexible. In some embodiments, the tubular member has sufficient flexibility such that it can be kneadable by hand. In some embodiments, the exterior surface and the interior surface of the tubular member are kneadable. In some embodiments, the tubular member can be made from a material having a modulus of elasticity from about $1 \times -10^2$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$. In some embodiments, the tubular member can be made from polyethylene terephthalate (PET) and has a modulus of elasticity of about $3.15 \times 10^8$ dynes/cm$^2$. In some embodiments, the tubular member is flexible when kneaded by hand. In some embodiments, the tubular member is able to resist stretching.

Figure 6:
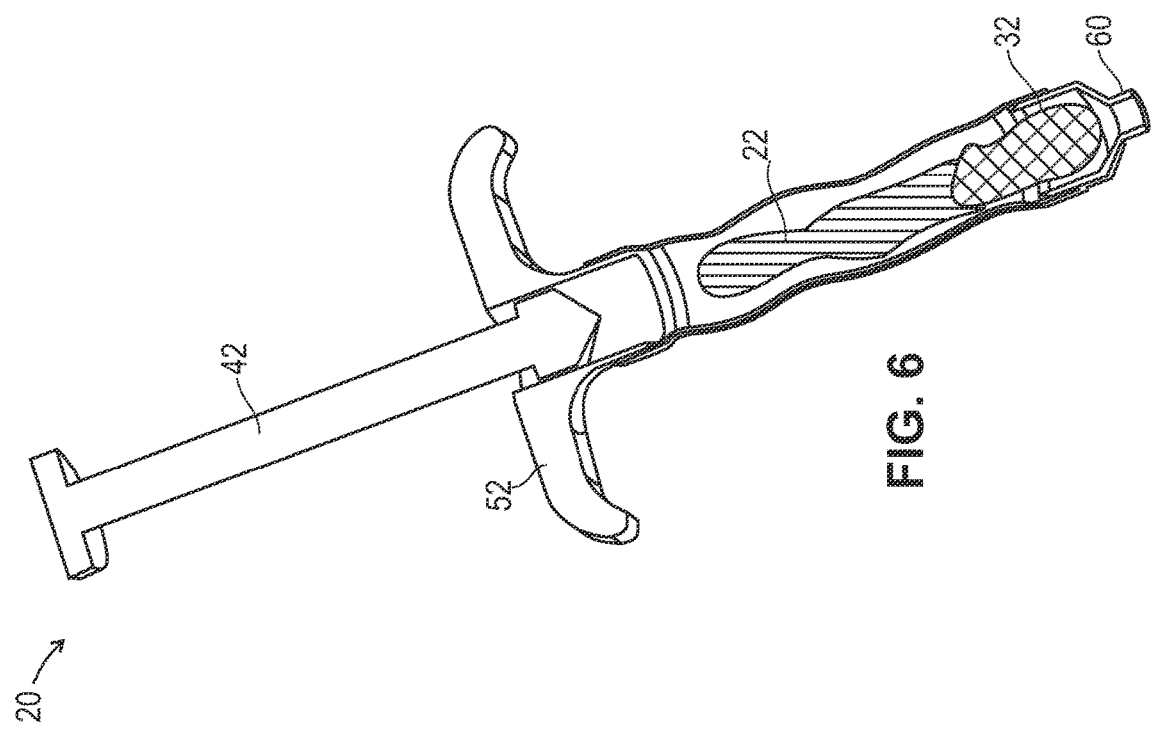
FIG. 6 is a perspective cross sectional view of the device of FIG. 1 preloaded with bone material and where a fluid has been inserted into the device through the distal opening of the tubular member.
Figure 10:
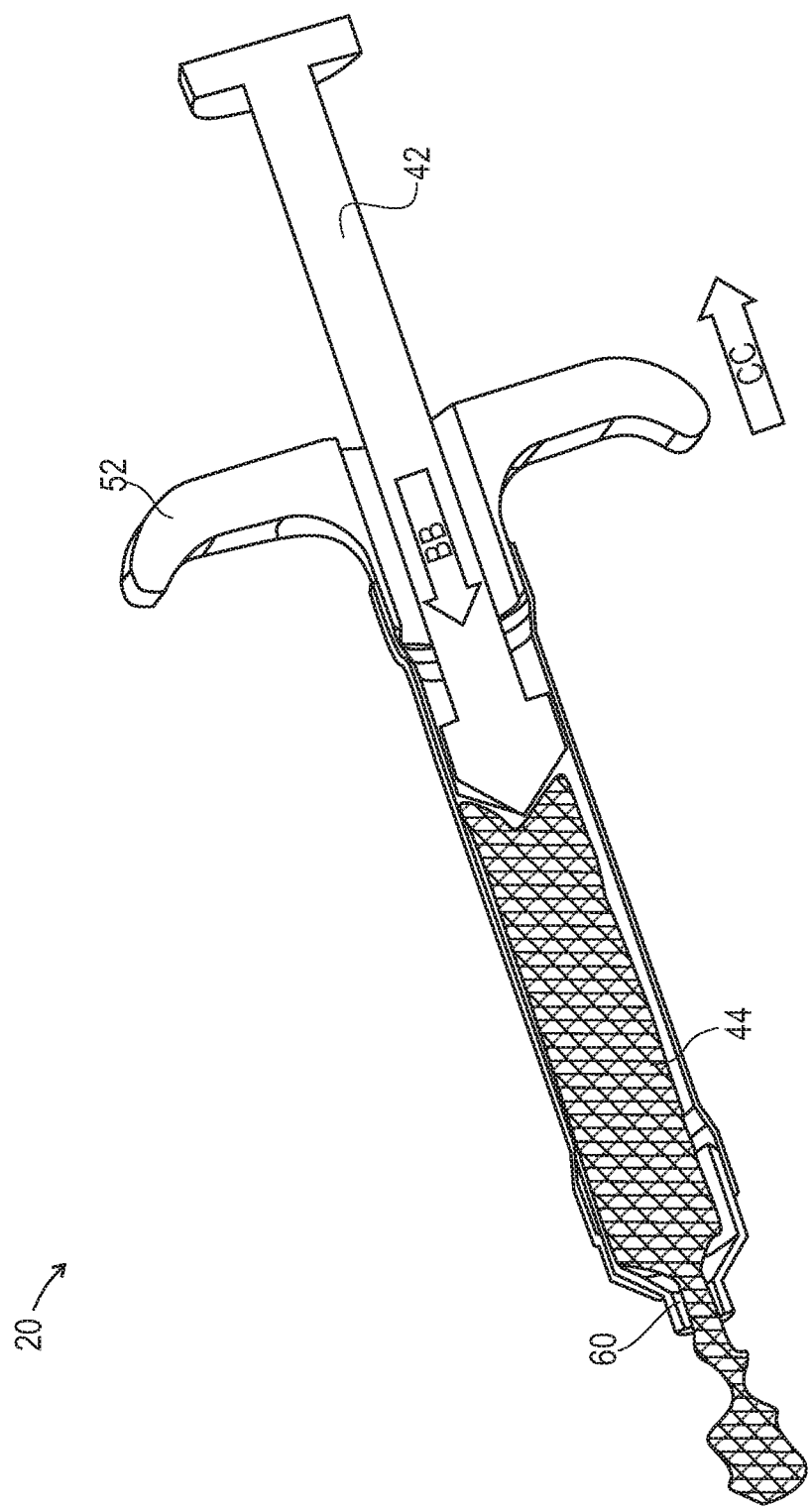
FIG. 10 is a perspective cross sectional view of the device of FIG. 7. The plunger is moved in a downward direction toward the distal opening of the tubular member to straighten the device. When the device is straightened, a seal is maintained between the tubular member and the plunger, and the bone material is dispensed from the distal opening of the tubular member.

To operate the device, as shown in FIGS. 5-10, the plunger engages with the opening of the handle and is in a resting position, as shown in FIG. 5. Dry bone material is preloaded within the chamber of the tubular member with either a frangible capsule filled with fluid (FIG. 5) or without a frangible capsule filled with fluid (FIG. 6.). When fluid is not located in a frangible capsule, or above the frangible barrier as shown in FIG. 3, the fluid, such as blood, bone marrow aspirate, saline, PBS, water etc. is inserted through the opening located at the distal end of the nozzle and the cap is then attached to the distal end of the nozzle. The tubular member is then kneaded by a user, for example with the user's palm and fingers so that the bone material and the fluid mix together to form a mixed bone material, as shown in FIGS. 7-10. Alternatively, when the fluid is disposed in the frangible capsule, the frangible capsule is broken when the user kneads the tubular member. When the tubular member includes a frangible barrier, the frangible barrier can be broken by kneading and/or by the plunger before the bone material and the fluid can be mixed. As shown in FIG. 10, the plunger is then moved in a downward, distal direction as shown by arrow BB. The pressure inside of the tubular member will straighten the syringe. The mixed bone material can then be dispensed from the distal end of the nozzle of the device and administered to a surgical site. In some embodiments, the tubular member does not stretch, and a seal is maintained between the plunger and the tubular member. The plunger can then be removed from the device by moving the plunger in an upward, proximal direction, as shown by arrow CC. The device can then be discarded or cleaned and reused.

In some embodiments, the fluid can be glycerol, blood, bone marrow aspirate, mesenchymal stem cells, sterile water, dextrose, other sugars including but not limited to sucrose, fructose, glucose, lactated ringer's, polyols including, but not limited to, mannitol, xylitol, sorbitol, maltitol, lactitol, polysaccharides including, but not limited to, native or pre-gelatinized starch, maltodextrins, cyclodextrins, mineral compounds including, but not limited to, dicalcium or tricalcium phosphate, either dihydrate or anhydrous, cellulose derivatives including, but not limited to, microcrystalline cellulose, lactoses either monohydrates thereof or anhydrous, as well as their mixtures such as dicalcium phosphate dihydrate, mannitol, pre-gelatinized maize starch, microcrystalline cellulose and their mixtures, water and/or NaCl (saline). In some embodiments, the saline is 0.90% saline, 0.45% saline or phosphate buffered saline. In some embodiments, other fluids can be used for example, D5W (dextrose in 5% water), D5NS (dextrose in 5% water and normal saline) and D5W/½NS (D5W and ½ normal saline), lactated Ringer solution or the like.

In some embodiments, the bone material can be in a powder or a wet form and has a particle size of 250 microns or less. In some embodiments, the bone material is demineralized bone (DBM). In some embodiments, the tubular member of the device can be pre-packed with the bone material in dry form from a manufacturer.

In some embodiments, components of the device can be fabricated from biologically acceptable materials suitable for medical applications, including metals, synthetic polymers, ceramics and/or their composites. For example, the components of the device, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetheketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, or any combination thereof.

In some embodiments, lubricants can be added to components of the device or can be added to the bone material. In some embodiments, lubricants can include biological lubricants such as, glycerol.

Bone Material

In some embodiments, the bone material can be made from natural bone and/or synthetic bone. In various embodiments, the bone material may be particulated such as, for example, in bone chips, powder or fiber form. In some embodiments, the bone material is in a powder or a wet form and has a particle size of 250 microns or less. In some embodiments, the bone material has a particle size of 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248 and/or 250 microns. In some embodiments, the bone material is demineralized bone (DBM).

If the bone is demineralized, the bone may be made into a particulate before, during or after demineralization. In some embodiments, the bone may be monolithic and may not be a particulate.

The bone may be milled and ground or otherwise processed into particles of an appropriate size before or after demineralization. The particles may be particulate (for example, powder) or fibrous. The terms milling or grinding are not intended to be limited to production of particles of a specific type and may refer to production of particulate or fibrous particles. In certain embodiments, the particle size may be greater than 25 microns, such as ranging from about 25 to about 250 microns, or from about 25 to about 200 microns or from about 25 to about 150 microns.

After grinding, the bone particles may be sieved to select those particles of a desired size. In certain embodiments, the particles may be sieved though a 25 micron sieve, a 50 micron sieve, a 75 micron sieve, a 100 micron sieve, a 125 micron sieve, a 150 micron sieve, a 175 micron sieve and/or a 200 micron sieve.

In some embodiments, the bone material comprises DBM and/or mineralized bone. In some embodiments, the size of the bone material is less than 25, 50, 75, 100, 125, 150, 175, 200 or 250 microns.

Following shaving, milling or other technique whereby they are obtained, the bone material is subjected to demineralization in order to reduce its inorganic content to a very low level, in some embodiments, to not more than about 5% by weight of residual calcium and to not more than about 1% by weight of residual calcium. Demineralization of the bone material ordinarily results in its contraction to some extent.

Bone used in the methods described herein may be autograft, allograft, or xenograft. In various embodiments, the bone may be cortical bone, cancellous bone, or corticocancellous bone. While specific discussion is made herein to demineralized bone matrix, bone matrix treated in accordance with the teachings herein may be non-demineralized, demineralized, partially demineralized, or surface demineralized. This discussion applies to demineralized, partially demineralized, and surface demineralized bone matrix. In one embodiment, the demineralized bone is sourced from bovine or human bone. In another embodiment, demineralized bone is sourced from human bone. In one embodiment, the demineralized bone is sourced from the patient's own bone (autogenous bone). In another embodiment, the demineralized bone is sourced from a different animal (including a cadaver) of the same species (allograft bone).

Any suitable manner of demineralizing the bone may be used. Demineralization of the bone material can be conducted in accordance with known conventional procedures. For example, in a preferred demineralization procedure, the bone materials useful for the implantable composition of this application are subjected to an acid demineralization step that is followed by a defatting/disinfecting step. The bone material is immersed in acid over time to effect its demineralization. Acids which can be employed in this step include inorganic acids such as hydrochloric acid and organic acids such as peracetic acid, acetic acid, citric acid, or propionic acid. The depth of demineralization into the bone surface can be controlled by adjusting the treatment time, temperature of the demineralizing solution, concentration of the demineralizing solution, agitation intensity during treatment, and other applied forces such as vacuum, centrifuge, pressure, and other factors such as known to those skilled in the art. Thus, in various embodiments, the bone material may be fully demineralized, partially demineralized, or surface demineralized.

After acid treatment, the bone is rinsed with sterile water for injection, buffered with a buffering agent to a final predetermined pH and then finally rinsed with water for injection to remove residual amounts of acid and buffering agent or washed with water to remove residual acid and thereby raise the pH. Following demineralization, the bone material is immersed in solution to effect its defatting. A defatting/disinfectant solution is an aqueous solution of ethanol, the ethanol being a good solvent for lipids and the water being a good hydrophilic carrier to enable the solution to penetrate more deeply into the bone. The aqueous ethanol solution also disinfects the bone by killing vegetative microorganisms and viruses. Ordinarily at least about 10 to 40 weight percent by weight of water (i.e., about 60 to 90 weight percent of defatting agent such as alcohol) should be present in the defatting/disinfecting solution to produce optimal lipid removal and disinfection within the shortest period of time. The concentration range of the defatting solution is from about 60 to 85 weight percent alcohol or about 70 weight percent alcohol.

Further in accordance with this application, the DBM material can be used immediately for preparation of the bone implant or it can be stored under aseptic conditions, advantageously in a critical point dried state prior to such preparation. In one embodiment, the bone material can retain some of its original mineral content such that the composition is rendered capable of being imaged utilizing radiographic techniques.

In various embodiments, this application also provides bone matrix compositions comprising critical point drying (CPD) fibers. DBM includes the collagen matrix of the bone together with acid insoluble proteins including bone morphogenic proteins (BMPs) and other growth factors. It can be formulated for use as granules, gels, sponge material or putty and can be freeze-dried for storage. Sterilization procedures used to protect from disease transmission may reduce the activity of beneficial growth factors in the DBM. DBM provides an initial osteoconductive matrix and exhibits a degree of osteoinductive potential, inducing the infiltration and differentiation of osteoprogenitor cells from the surrounding tissues.

DBM preparations have been used for many years in orthopedic medicine to promote the formation of bone. For example, DBM has found use in the repair of fractures, in the fusion of vertebrae, in joint replacement surgery, and in treating bone destruction due to underlying disease such as rheumatoid arthritis. DBM is thought to promote bone formation in vivo by osteoconductive and osteoinductive processes. The osteoinductive effect of implanted DBM compositions is thought to result from the presence of active growth factors present on the isolated collagen-based matrix. These factors include members of the TGF-$\beta$, IGF, and BMP protein families. Particular examples of osteoinductive factors include TGF-$\beta$, IGF-1, IGF-2, BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors present in DBM.

In various embodiments, the DBM provided in this application can be prepared from elongated bone fibers which have been subjected to critical point drying (CPD). The elongated CPD bone fibers employed in this application are generally characterized as having relatively high average length to average width ratios, also known as the aspect ratio. In various embodiments, the aspect ratio of the elongated bone fibers is at least from about 50:1 to at least about 1000:1. Such elongated bone fibers can be readily obtained by any one of several methods, for example, by milling or shaving the surface of an entire bone or relatively large section of bone.

In other embodiments, the length of the fibers can be at least about 3.5 cm and average width from about 20 mm to about 1 cm. In various embodiments, the average length of the elongated fibers can be from about 3.5 cm to about 6.0 cm and the average width from about 20 mm to about 1 cm. In other embodiments, the elongated fibers can have an average length from about 4.0 cm to about 6.0 cm and an average width from about 20 mm to about 1 cm.

In some embodiments, the elongated fibers can be the length of the tubular member and can be folded when placed in the tubular member. In some embodiments, the kneading of the tubular member can break the elongated fibers into shorter segments. In some embodiments, the elongated fibers or fibers can be provided loose or in a single brick such that kneading of the tubular member not only integrates the fluid among the fibers but also breaks the clump of fibers into smaller pieces.

In yet other embodiments, the diameter or average width of the elongated fibers is for example, not more than about 1.00 cm, not more than 0.5 cm or not more than about 0.01 cm. In still other embodiments, the diameter or average width of the fibers can be from about 0.01 cm to about 0.4 cm or from about 0.02 cm to about 0.3 cm.

In another embodiment, the aspect ratio of the fibers n be from about 50:1 to about 950:1, from about 50:1 to about 750:1, from about 50:1 to about 500:1, from about 50:1 to about 250:1; or from about 50:1 to about 100:1. Fibers according to this disclosure can have an aspect ratio from about 50:1 to about 1000:1, from about 50:1 to about 950:1, from about 50:1 to about 750:1, from about 50:1 to about 600:1, from about 50:1 to about 350:1, from about 50:1 to about 200:1, from about 50:1 to about 100:1, or from about 50:1 to about 75:1.

In some embodiments, the chips to fibers ratio is about 90:10, 80:20, 75:25, 70:30, 60:40, 50:50, 40:60, 30:70, 25:75, 20:80 and/or 10:90. In various embodiments, a surface demineralized chips to fibers ratio is about 90:10, 80:20, 75:25, 70:30, 60:40, 50:50, 40:60, 30:70, 25:75, 20:80 and/or 10:90. In some embodiments, a surface demineralized chips to fully demineralized fibers ratio is about 90:10, 80:20, 75:25, 70:30, 60:40, 50:50, 40:60, 30:70, 25:75, 20:80 and/or 10:90.

In some embodiments, the DBM fibers have a thickness of about 0.5-4 mm. In various embodiments, the DBM fibers have a thickness of about 0.5, 0.6, 0.7, 0.8, 0.9, 1, 1.5, 2, 2.5, 3, 3.5 and/or 4 mm. In various embodiments, the ratio of DBM fibers to DBM powder is about 40:60 to about 90:10 W/W, W/V or V/V. In some embodiments, the ratio of mineralized bone fibers to DBM powder is about 25:75 to about 75:25 W/W, W/V or V/V. In various embodiments, the bone implant comprises DBM fibers and mineralized fibers in a ratio of 40:60 to about 90:10 W/W, W/V or V/V. In some embodiments, the DBM fibers to DBM powder ratio, mineralized bone fibers to DBM powder ratio and/or the DBM fibers and mineralized fibers ratio is from 5:95 to about 95:5 W/W, W/V or V/V. In some embodiments, the DBM fibers to DBM powder ratio, mineralized bone fibers to DBM powder ratio and/or the DBM fibers and mineralized fibers ratio is 5:95, 10:90, 15:85, 20:80, 25:75, 30:70, 35:65, 40:60, 45:55, 50:50, 55:45, 60:40, 65:35, 70:30, 75:25, 80:20, 85:15, 90:10 and/or 95:5 W/W, W/V or V/V.

In some embodiments, the bone material comprises demineralized bone material comprising demineralized bone, fibers, powder, chips, triangular prisms, spheres, cubes, cylinders, shards or other shapes having irregular or random geometries. These can include, for example, "substantially demineralized," "partially demineralized," or "fully demineralized" cortical and/or cancellous bone. These also include surface demineralization, where the surface of the bone construct is substantially demineralized, partially demineralized, or fully demineralized, yet the body of the bone construct is fully mineralized.

In various embodiments, the bone material comprises fully DBM fibers and surface demineralized bone chips. In some embodiments, the ratio of fully DBM fibers to surface demineralized bone chips is from 5:95 to about 95:5 fibers to chips. In some embodiments, the ratio of fully DBM fibers to surface demineralized bone chips is 5:95, 10:90, 15:85, 20:80, 25:75, 30:70, 35:65, 40:60, 45:55, 50:50, 55:45, 60:40, 65:35, 70:30, 75:25, 80:20, 85:15, 90:10 and/or 95:5 fibers to chips. In various embodiments, the fully DBM fibers have a thickness of about 0.5-4 mm. In various embodiments, the fully DBM fibers have a thickness of about 0.5, 0.6, 0.7, 0.8, 0.9, 1, 1.5, 2, 2.5, 3, 3.5 and/or 4 mm.

In various embodiments, the fibers and/or the powder is surface DBM. In some embodiments, the fibers and/or the powder is surface DBM cortical allograft. In various embodiments, surface demineralization involves surface demineralization to at least a certain depth. For example, the surface demineralization of the allograft can be from about 0.25 mm, 0.5 mm, 1 mm, 1.5 mm, 2.0 mm, 2.5 mm, 3.0 mm. 3.5 mm, 4 mm, 4.5 mm, to about 5 mm. The edges of the bone fibers and/or powder may further be machined into any shape or to include features such as grooves, protrusions, indentations, etc., to help improve fit and limit any movement or micromotion to help fusion and/or osteoinduction to occur.

To prepare the osteogenic DBM, a quantity of fibers is combined with a biocompatible carrier to provide a demineralized bone matrix.

DBM typically is dried, for example via lyophilization or solvent drying, to store and maintain the DBM in active condition for implantation. Moreover, each of these processes is thought to reduce the overall surface area structure of bone. As may be appreciated, the structural damage of the exterior surface reduces the overall surface area. Physical alterations to the surface and reduction in surface area can affect cell attachment, mobility, proliferation, and differentiation. The surface's affinity for growth factors and release kinetics of growth factors from the surface may also be altered.

Accordingly, in some embodiments, methods for drying bone to store and maintain the bone in active condition for implantation that maintains or increases the surface area of the bone are provided. In one embodiment, the bone matrix is treated using a critical point drying technique, thereby reducing destruction of the surface of the bone. While specific description is made to critical point drying, it is to be appreciated that, in alternative embodiments, super critical point treatment may be used. In various embodiments utilizing CPD, a percentage of collagen fibrils on the surface of the bone are non-denatured after drying to a residual moisture content of approximately 15% or less. In some embodiments, after drying, the bone matrix has a residual moisture content of approximately 8% or less. In some embodiments, after drying, the bone matrix has a residual moisture content of approximately 6% or less. In some embodiments, after drying, the bone matrix has a residual moisture content of approximately 3% or less.

Evaporative drying and freeze drying of specimens can cause deformation and collapse of surface structures, leading to a decrease in surface area. Without wishing to be bound by a particular theory, this deformation and structure is thought to occur because as a substance crosses the boundary from liquid to gas, the substance volatilizes such that the volume of the liquid decreases. As this happens, surface tension at the solid-liquid interface pulls against any structures to which the liquid is attached. Delicate surface structures tend to be broken apart by this surface tension. Such damage may be caused by the effects of surface tension on the liquid/gas interface. Critical point drying is a technique that avoids effects of surface tension on the liquid/gas interface by substantially preventing a liquid/gas interface from developing. Critical point or supercritical drying does not cross any phase boundary, instead passing through the supercritical region, where the distinction between gas and liquid ceases to apply. As a result, materials dehydrated using critical point drying are not exposed to damaging surface tension forces. When the critical point of the liquid is reached, it is possible to pass from liquid to gas without abrupt change in state. Critical point drying can be used with bone matrices to phase change from liquid to dry gas without the effects of surface tension. Accordingly, bone dehydrated using critical point drying can retain or increase at least some of the surface structure and therefore the surface area.

In some embodiments, critical point drying is carried out using carbon dioxide. However, other mediums such as Freon, including Freon 13 (chlorotrifluoromethane), may be used. Generally, fluids suitable for supercritical drying include carbon dioxide (critical point 304.25 K at 7.39 MPa or 31.1° C. at 1072 psi or 31.2° C. and 73.8 bar) and Freon (about 300 K at 3.5-4 MPa or 25 to 30° C. at 500-600 psi). Nitrous oxide has similar physical behavior to carbon dioxide, but is a powerful oxidizer in its supercritical state. Supercritical water is also a powerful oxidizer, partly because its critical point occurs at such a high temperature (374° C.) and pressure (3212 psi/647 K and 22.064 MPa).

In some embodiments, the bone may be pretreated to remove water prior to critical point drying. Thus, in accordance with one embodiment, bone matrix is dried using carbon dioxide in (or above) its critical point status. After demineralization, bone matrix samples (in water) may be dehydrated to remove residual water content. Such dehydration may be, for example, through a series of graded ethanol solutions (for example, 20%, 50%, 70%, 80%, 90%, 95%, 100% ethanol in deionized water). In some embodiments, penetrating the tissue with a graded series of ethanol solutions or alcohols may be accomplished in an automated fashion. For example, pressure and vacuum could be used to accelerate penetration into the tissue.

Device Materials

In some embodiments, the device can be made from a natural and/or synthetic material such as, for example, poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, L-lactide-co-ε-caprolactone, polydioxanone (PDO), allogeneic collagen, xenogenic collagen, metals such as titanium/titanium alloys, TiNi (shape memory/super elastic), aluminum oxide, platinum/platinum alloys, stainless steels, and other metal alloys known to be useful for medical devices, pyrolytic carbon, silver or glassy carbon; polymers such as polyurethanes, polycarbonates, silicone elastomers, polyolefins including polyethylenes or polypropylenes (such as found in hernia mesh substrates and suture materials), polyvinyl chlorides, polyethers, polyesters, nylons, polyvinyl pyrrolidones, polyacrylates and polymethacrylates such as polymethylmethacrylate (PMMA), n-Butyl cyanoacrylate, polyvinyl alcohols, polyisoprenes, rubber, cellulosics, polyvinylidene fluoride (PVDF), polytetrafluoroethylene, ethylene tetrafluoroethylene copolymer (ETFE), acrylonitrile butadiene ethylene, polyamide, polyimide, styrene acrylonitrile, and the like; minerals or ceramics such as hydroxapatite; human or animal protein or tissue such as bone, skin, teeth, collagen, laminin, elastin or fibrin; organic materials such as wood, cellulose, or compressed carbon; and other materials such as glass or a combination thereof.

The device can be made from additive manufacturing methods (e.g., 3D printing). In some embodiments, the components of the device, such as the tubular member can be made from an impermeable yarn that is monofilament or multifilament, and the yarn can be knitted, woven, non-woven shape memory, felted, point-bonded, additive manufactured, such as 3-D printed or a combination thereof. A weave pattern can be selected to impart flexibility and stretchable characteristics to the tubular member.

The average molecular weight of the polymer used to make the tubular member can be from about 1,000 to about 10,000,000; or about 1,000 to about 1,000,000; or about 5,000 to about 500,000; or about 10,000 to about 100,000; or about 20,000 to 50,000 g/mol. In some embodiments, the molecular weight of the polymer is 1,000, 2,000, 3,000, 4,000, 5,000, 6,000, 7,000, 8,000, 9,000, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, 125,000, 150,000, 175,000, 200,000, 225,000, 250,000, 275,000, 300,000, 325,000, 350,000, 375,000, 400,000, 425,000, 450,000, 475,000, 500,000, 525,000, 550,000, 575,000, 600,000, 625,000, 650,000, 675,000, 700,000, 725,000, 750,000, 775,000, 800,000, 825,000, 850,000, 875,000, 900,000, 925,000, 950,000, 975,000 and/or 1,000,000 Daltons.

In some embodiments, the tubular member can be made from threads and can have a predetermined thickness of about 0.01 mm to about 2.0 mm, about 0.05 mm to about 1.0 mm, or about 0.1 to about 0.5 mm. The thickness of the threads may be uniform along the length of each thread, or varied across the length of each thread. In some embodiments, some threads have a greater thickness than other threads. The threads may be sized to allow for customizable pore sizes between the threads.

Suitable adhesives for use for engaging the handle and/or the nozzle to the tubular member may include, for example, cyanoacrylates (such as histoacryl, B Braun, which is n-butyl-2 cyanoacrylate; or Dermabond, which is 2-octyl-cyanoacrylate); epoxy-based compounds, dental resin sealants, dental resin cements, glass ionomer cements, polymethyl methacrylate, gelatin-resorcinol-formaldehyde glues, collagen-based glues, inorganic bonding agents such as zinc phosphate, magnesium phosphate or other phosphate-based cements, zinc carboxylate, L-DOPA (3,4-dihydroxy-L-phenylalanine), proteins, carbohydrates, glycoproteins, mucopolysaccharides, other polysaccharides, hydrogels, protein-based binders such as fibrin glues and mussel-derived adhesive proteins, and any other suitable substance. Adhesives may be selected for use based on their bonding time; for example, in some circumstances, a temporary adhesive may be desirable, while in other circumstances a permanent adhesive may be desired.

In accordance with some embodiments, the bone material to be loaded in the tubular member may be supplemented, further treated, or chemically modified with one or more bioactive agents or bioactive compounds. Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides; DBM powder; collagen, insoluble collagen derivatives, etc., and soluble solids and/or liquids dissolved therein; anti-AIDS substances; anti-cancer substances; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; antispasmodics and muscle contractants including channel blockers; miotics and anti-cholinergics; anti-glaucoma compounds; anti-parasite and/or anti-protozoal compounds; modulators of cell-extracellular matrix interactions including cell growth inhibitors and antiadhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anticoagulants and/or antithrombotic agents; local anesthetics; ophthalmics; prostaglandins; anti-depressants; anti-psychotic substances; anti-emetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases and the like; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other member; tissue transplants; autogenous tissues such as blood, blood aspirate, serum, soft tissue, bone marrow, or the like; bioadhesives; bone morphogenetic proteins (BMPs including BMP-2); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, for example, interleukin-1 (IL-1), interleukin-2 (IL-2); human alpha thrombin; transforming growth factor (TGF-beta); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, for example, fatty acid esters such as laureate, myristate and stearate monoesters of polyethylene glycol, enamine derivatives, alpha-keto aldehydes; and nucleic acids.

In certain embodiments, the bioactive agent may be a drug. In some embodiments, the bioactive agent may be a growth factor, cytokine, extracellular matrix molecule, or a fragment or derivative thereof, for example, a protein or peptide sequence such as RGD.

The material may have functional characteristics. Alternatively, other materials having functional characteristics may be incorporated into the mesh material. Functional characteristics may include radiopacity, bacteriocidity, source for released materials, tackiness, etc. Such characteristics may be imparted substantially throughout the mesh material and/or mesh body or at only certain positions or portions of the mesh material and/or mesh body.

Suitable radiopaque materials that can be added to the particulate bone material include, for example, ceramics, mineralized bone, ceramics/calcium phosphates/calcium sulfates, metal particles, fibers, and iodinated polymer (see, for example, WO/2007/143698). Suitable bacteriocidal materials may include, for example, trace metallic elements. In some embodiments, trace metallic elements may also encourage bone growth.

Kit

In various embodiments, a kit can be provided containing the device prefilled with bone material and/or fluid or the kit can contain the device. In some embodiments, the kit may include additional parts along with the device such as the bone material (e.g., bone graft) fluid and dilators (e.g., wipes, needles, etc.). The kit may include the device in a first compartment. The second compartment may include the fluid sealed in a container, along with a vial containing diluent and any other delivery instruments needed for the localized delivery. A third compartment may include gloves, drapes, wound dressings and other procedural supplies for maintaining sterility of the implanting process, as well as an instruction booklet, which may include a chart that shows how to implant the bone material. A fourth compartment may include additional needles, fasteners, and/or sutures. Each tool may be separately packaged in a plastic pouch that is radiation sterilized. A fifth compartment may include an agent for radiographic imaging. A cover of the kit may include illustrations of the implanting procedure and a clear plastic cover may be placed over the compartments to maintain sterility.

Methods

A method of mixing and dispensing bone material is provided. The devices and bone material used in this method can be found in FIGS. 1-10. The method can be employed with various delivery instrument and in a surgical treatment with a patient in a prone or supine position, and/or employ various surgical approaches to the spine, including anterior, posterior, posterior mid-line, direct lateral, and/or anterolateral approaches, and in other body regions. The method may also be employed with procedures for treating the lumbar, cervical, thoracic, sacral and pelvic regions of a spinal column. The method may also be used on animals, bone models and other non-living substrates, such as, for example, in training, testing and demonstration.

The method comprises employing a device comprising a tubular member having an interior surface configured to receive bone material and a fluid to mix the bone material disposed within the tubular member, the interior surface containing the bone material and the fluid separated by a frangible barrier disposed on the interior surface, the frangible barrier configured to break and allow mixing of the fluid with the bone material, the tubular member being flexible and having a proximal opening configured to slidably receive a plunger, and a distal opening configured to dispense a mixed bone material from the interior surface of the tubular member, the tubular member being less flexible than the frangible barrier; inserting the plunger into the proximal opening of the tubular member; inserting fluid into the tubular member at the distal opening; breaking the frangible barrier with the plunger; kneading the tubular member to mix the bone material and the fluid to create a mixed bone material; and moving the plunger in a downward direction toward the distal opening of the tubular member to dispense the mixed bone material.

In some embodiments, the plunger comprises a proximal end and a distal end, the distal end having an angled tip, the angled tip configured to break the frangible barrier. In some embodiments, the tubular member has sufficient flexibility to be kneadable by hand.

The bone material may be used in a minimally invasive procedure via placement through a small incision, via delivery through the dilators, or other means. The size and shape may be designed with restrictions on delivery conditions. For example, the bone material may be percutaneously delivered to the surgical site, and in some cases, the surgical site is the posterior spine.

In some embodiments, the bone material may be used in healing vertebral compression fractures, interbody fusion, minimally invasive procedures, posterolateral fusion, correction of adult or pediatric scoliosis, treating long bone defects, osteochondral defects, ridge augmentation (dental/craniomaxillofacial, e.g. edentulous patients), beneath trauma plates, tibial plateau defects, filling bone cysts, wound healing, around trauma, contouring (cosmetic/plastic/reconstructive surgery), and others.

Generally, the bone material may be applied to a pre-existing defect, to a created channel, or to a modified defect. Thus, for example, a channel may be formed in a bone, or a pre-existing defect may be cut to form a channel, for receipt of the bone material. The bone material may be configured to match the channel or defect. In some embodiments, the configuration of bone material may be chosen to match the channel. In other embodiments, the channel may be created, or the defect expanded or altered, to reflect a configuration of the bone material. The bone material may be placed in the defect or channel and, optionally, coupled using attachment mechanisms.

Although the invention has been described with reference to embodiments, persons skilled in the art will recognize that changes may be made in form and detail without departing from the spirit and scope of the invention.

What is claimed is:

1. A device for mixing and dispensing bone material, the device comprising a tubular member having an interior surface configured to receive bone material and a fluid to mix the bone material disposed within the tubular member, the tubular member being flexible and having a proximal end defining a proximal opening configured to slidably receive a plunger, and a distal end defining a distal opening configured to dispense a mixed bone material from the interior surface of the tubular member, the plunger being less flexible than the tubular member, wherein the tubular member has a portion extending from the proximal end to the distal end such that the portion has sufficient flexibility to be kneadable by hand to mix the bone material disposed within the interior surface of the tubular member.

2. The device of claim 1, wherein the tubular member comprises a proximal end having a handle, the handle being less flexible than the tubular member.

3. The device of claim 2, wherein the handle has an opening configured to slidably receive the plunger, the opening aligning with the proximal opening of the tubular member.

4. The device of claim 1, wherein the tubular member comprises a distal end having a nozzle to dispense the mixed bone material, the nozzle being less flexible than the tubular member.

5. The device of claim 4, wherein the nozzle has an interior surface comprising at least one projection for mixing and/or dispensing the mixed bone material.

6. The device of claim 4, wherein the nozzle is configured to receive a cap to hold the mixed bone material within the interior surface of the tubular member.

7. The device of claim 1, wherein the interior surface comprises bone material and a mixing space to receive the fluid to mix with the bone material.

8. The device of claim 1, wherein the tubular member comprises an exterior surface, and the interior surface and the exterior surface of the tubular member are both kneadable by hand.

9. The device of claim 1, wherein (i) the fluid is disposed in a frangible capsule within the tubular member; (ii) the bone material is disposed in a frangible capsule within the tubular member; or (iii) the interior surface of the tubular member comprises a frangible barrier configured to separate the bone material from the fluid and to break to allow mixing of the fluid with the bone material.

10. The device of claim 9, wherein the frangible capsule is attached to the plunger.

11. The device of claim 1, wherein the bone material comprises natural bone or synthetic bone and the fluid comprises blood, bone marrow aspirate, saline, phosphate buffered saline, or sterile water.

12. A device for mixing and dispensing bone material, the device comprising a tubular member having an interior surface configured to receive bone material and a fluid to mix the bone material disposed within the tubular member, the interior surface comprising a frangible barrier, the frangible barrier configured to separate the bone material from the fluid and to break to allow mixing of the fluid with the bone material, the tubular member being flexible and having a proximal end defining a proximal opening configured to slidably receive a plunger, and a distal end defining a distal opening configured to dispense a mixed bone material from the interior surface of the tubular member, the tubular member being less flexible than the frangible barrier, wherein the tubular member has a portion extending from the proximal end to the distal end such that the portion has sufficient flexibility to be kneadable by hand to mix the bone material disposed within the interior surface of the tubular member.

13. The device of claim 10, wherein the plunger is less flexible than the tubular member.

14. The device of claim 13, wherein the plunger comprises a proximal end and a distal end, the distal end having an angled tip, the angled tip configured to break the frangible barrier.

15. The device of claim 10, wherein the tubular member comprises a proximal end having a handle, the handle having an opening aligning with the proximal opening of the tubular member, and the handle being less flexible than the tubular member.

16. The device of claim 10, wherein the tubular member comprises a distal end having a nozzle to dispense the mixed bone material, the nozzle being less flexible than the tubular member, and the nozzle having an interior surface comprising at least one projection for mixing and/or dispensing the mixed bone material.

17. The device of claim 16, wherein (i) the tubular member comprises an exterior surface, and the interior surface and the exterior surface of the tubular member are both kneadable by hand; and (ii) the nozzle is configured to receive a cap to hold the mixed bone material within the interior surface of the tubular member.

18. A device for mixing and dispensing bone material, the device comprising a tubular member having an interior surface configured to receive bone material and a fluid to mix the bone material disposed within the tubular member, the tubular member being flexible and having a proximal end defining a proximal opening configured to slidably receive a plunger, and a distal end defining a distal opening configured to dispense a mixed bone material from the interior surface of the tubular member, the plunger being less flexible than the tubular member, wherein a frangible barrier is positioned vertically within the tubular member such that sealed compartments within the tubular member are formed, wherein the tubular member has a portion extending from the proximal end to the distal end such that the portion has sufficient flexibility to be kneadable by hand to mix the bone material disposed within the interior surface of the tubular member.

* * * * *